United States Patent [19]

Achard et al.

[11] Patent Number: 5,463,077
[45] Date of Patent: Oct. 31, 1995

[54] PERHYDROISOINDOLE DERIVATIVES AND PREPARATION

[75] Inventors: Daniel Achard, Thiais; Serge Grisoni, Choisy-le-Roi; Jean-Luc Malleron, Marcoussis; Jean-Francois Peyronel, Palaiseau; Michel Tabart, Paris, all of France

[73] Assignee: Rhone-Poulenc Rorer S.A., Antony, France

[21] Appl. No.: 313,120

[22] PCT Filed: Apr. 8, 1993

[86] PCT No.: PCT/FR93/00351

§ 371 Date: Oct. 11, 1994

§ 102(e) Date: Oct. 11, 1994

[87] PCT Pub. No.: WO93/21154

PCT Pub. Date: Oct. 28, 1993

[30] Foreign Application Priority Data

Apr. 10, 1992 [FR] France .................................. 92/04391

[51] Int. Cl.$^6$ .................................................. C07D 209/04
[52] U.S. Cl. .................................................. 548/515
[58] Field of Search ............................ 548/515; 514/412

[56] References Cited

U.S. PATENT DOCUMENTS

| | | | |
|---|---|---|---|
| 4,042,707 | 8/1977 | Ripka | 424/489 |
| 5,006,534 | 4/1991 | Mohrs et al. | 424/489 |
| 5,102,667 | 4/1992 | Dubroeucq et al. | 424/489 |

FOREIGN PATENT DOCUMENTS

| | | | |
|---|---|---|---|
| 429366 | 5/1991 | European Pat. Off. | 424/489 |
| 430771 | 6/1991 | European Pat. Off. | 424/489 |
| 514274 | 11/1992 | European Pat. Off. | 424/489 |

OTHER PUBLICATIONS

CA 120:244664g Preparation . . . antagonists. Achard et al., p. 1002, 1994.
J. Am. Chem. Soc., 96, Olah et al., Synthetic . . . Anhydrides, pp. 925–927, 1974.
J. Am. Chem. Soc., 84, Sheppard, Alkyl–. . . Trifluorides, pp. 3058–3063, 1962.
Tetrahedron Letters, 12, Guedj et al., Amines . . . Fluoro, pp. 907–910, 1973.
J. Org. Chem., 40, Kollonitsch et al., Selective . . . Fluoride, pp. 3808–3809, No. 25, 1975.
Tetrahedron, 44, No. 10, Hamatani et al., A Stereocontrolled . . . Difluoroalkanes pp. 2875–2880, 1988.

Primary Examiner—Joseph K. McKane
Attorney, Agent, or Firm—Morgan & Finnegan

[57] ABSTRACT

This ivention relates to novel perhydroisoindole derivatives having formula (I),

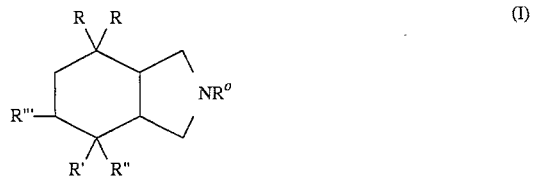

wherein the symbols R, which are the same or different, are phenyl radicals optionally 2- or 3-substituted by a halogen atom or a methyl radical, R' is a phenyl radical optionally 2-substituted by a $C_{1-2}$ alkylk or alkyloxy radical, R" is a fluorine atom or a hydroxy radical, and R''' is a hydrogen atom, or else R' and R''' are hydroxy radicals, or R" and R''' together form a bond, and $R^o$ is a hydrogen atom or a protective radical; salts thereof whereever applicable; and preparation thereof. These products are synthetic intermediates for the preparation of derivatives having P substance antagonist activity.

4 Claims, No Drawings

PERHYDROISOINDOLE DERIVATIVES AND PREPARATION

This application is a 371 of PCT/FR 93/00351 filed Apr. 8, 1993.

1. Field of the Invention

The present invention relates to new perhydroisoindole derivatives of the general formula:

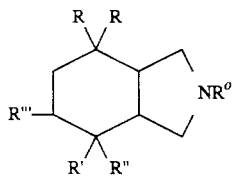

(I)

in which:

the symbols R are identical and represent phenyl radicals which are optionally substituted by a halogen atom or by a methyl radical in position 2 or 3, the symbol R' represents a phenyl radical which is optionally substituted in position 2 by an alkyl or alkyloxy radical containing 1 or 2 carbon atoms, the symbol R" represents a fluorine atom or a hydroxyl radical and the symbol R''' represents a hydrogen atom, or the symbols R" and R''' represent hydroxyl radicals, or the symbol R" forms a bond with R''', and the symbol $R^o$ represents a hydrogen atom or represents a protective radical, and to their salts, where these exist, which are synthesis intermediates for the preparation of derivatives having an antagonistic activity against substance P.

2. BACKGROUND OF THE INVENTION

European Patent Application EP 430 771 has described perhydroisoindolone derivatives having the structure:

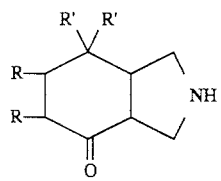

in which the symbols R are hydrogen or together form a bond and the symbols R' are phenyl radicals which are optionally substituted, which are intermediates for the preparation of perhydroisoindolone antagonists of substance P described in European Application EP 429 366. However, these perhydroisoindolone derivatives have been found to be active mainly in binding tests using homogenates of the rat brain, and show less activity in binding tests using cultured human lymphoblast cells.

U.S. Pat. No. 4,042,707 has described products derived from isoindole of the general formula:

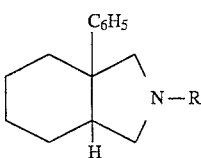

having an opiate activity. These products do not have any activity against substance P, and neither are they useful as intermediates.

In the general formula (I), if R carries a halogen substituent, this can be chosen from chlorine or fluorine.

The protective radical $R^o$ can be any compatible amino-protective group, the introduction and elimination of which does not change the remainder of the molecule. Examples which may be mentioned are the optionally substituted alkyloxycarbonyl, benzyloxycarbonyl and benzyl groups, and the formyl, chloroacetyl, trichloroacetyl, trifluoroacetyl, vinyloxycarbonyl, phenoxycarbonyl, 1-chloroethoxycarbonyl or chlorocarbonyl groups.

In addition, the products of the general formula (I) have different stereoisomeric forms, and it is understood that the racemic forms and the stereoisomeric forms having the structure:

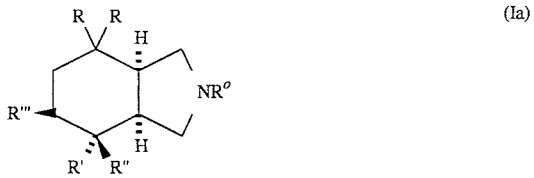

(Ia)

as well as their mixtures fall within the context of the present invention. More specifically, the present invention relates to the perhydroisoindole derivatives in which R" is hydroxyl or fluorine and R''' is hydrogen in the (3aS,4S,7aS) form in the pure state, or in the form of the racemic mixture (3aRS, 4RS,7aRS), the perhydroisoindole derivatives in which R" and R''' are hydroxyl in the (3aS,4S,5S,7aS) form in the pure state or in the form of the racemic mixture (3aRS,4RS,5RS, 7aRS) and the perhydroisoindole derivatives in which R" forms a bond with R''' in the (3aS,7aR) form in the pure state, or in the form of the racemic mixture (3aRS,7aSR).

DESCRIPTION OF THE INVENTION

According to the invention, the perhydroisoindole derivative of the general formula (I) may be obtained by the action of an organometallic compound of the general formula:

(II)

in which R' is as defined above and M represents lithium, an MgX or $CeX_2$ radical, in which X is a halogen atom, on the corresponding perhydroisoindolone derivative of the general formula:

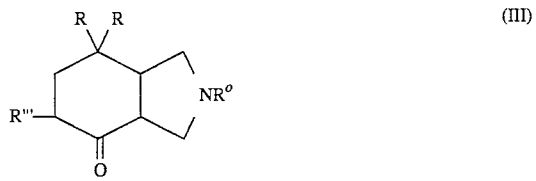

(III)

in which R is as defined above, R''' is a hydrogen atom or a hydroxyl radical, which is protected if appropriate, and $R^o$ is a protective radical as defined above, followed by liberation, where appropriate, of the protective radical of R''', then by conversion, where appropriate, of the product obtained in which R'' is a hydroxyl radical and R''' is a hydrogen atom into a product in which R'' is a fluorine atom and R''' is a hydrogen atom or into a product in which R'' and R''' together form a bond, and, where appropriate, removal of the protective radical $R^o$.

The protection of the radical R''' and the removal of the protective radical are carried out by the usual methods of protection and/or removal of hydroxyl radicals which do not change the remainder of the molecule.

The reaction is carried out in an anhydrous medium under the usual conditions for reaction of organometallic compounds with a ketone which do not affect the remainder of the molecule. In particular, the reaction is carried out in an ether (for example tetrahydrofuran or ethyl ether), if appropriate in the presence of anhydrous cerium chloride, at a temperature of between −78° and 30° C. It is understood that, according to the nature of the protective radical on the radical R''', this may be removed simultaneously with the reaction.

The isoindole derivative of the general formula (I) in which R'' is a fluorine atom and R''' is a hydrogen atom can be prepared by fluorination of an isoindole derivative of the general formula (I) in which R and R' are as defined above, $R^o$ is a protective radical, R'' is a hydroxyl radical and R''' is a hydrogen atom, and, where appropriate, removal of the protective radical $R^o$.

The reaction is advantageously carried out by means of a fluorinating agent, such as a sulphur fluoride [morpholinosulphur trifluoride, sulphur tetrafluoride (J. Org. Chem., 40, 3808 (1975)), diethylaminosulphur trifluoride (Tetrahedron, 44, 2875 (1988)) and phenylsulphur trifluoride (J. Am. Chem. Soc., 84, 3058 (1962)], selenium tetrafluoride (J. Am. Chem. Soc., 96, 925 (1974) or tetrafluorophenylphosphorane (Tet. Let., 907 (1973), working in an organic solvent, such as a chlorinated solvent (methylene chloride or dichloroethane, for example) at a temperature of between −30° and 30° C.

The perhydroisoindole derivative of the general formula (I) in which R'' and R''' together form a bond can be obtained by dehydration of the corresponding perhydroisoindole derivative of the general formula (I) in which R'' is a hydroxyl radical and R''' is a hydrogen atom, and R and $R^o$ are as defined above, and, where appropriate, removal of the protective radical $R^o$.

The reaction is carried out by any known method for dehydration of alcohols which does not change the remainder of the molecule. In particular, the dehydration is carried out in an acid medium, for example by the action of a sulphonic acid (p-toluenesulphonic acid and the like), sulphuric acid, phosphoric acid, phosphorus pentoxide or aluminium oxide, or by the action of a mixture of hydrochloric acid/acetic acid or hydrobromic acid/acetic acid, at a temperature of between 25° C. and the reflux temperature of the reaction mixture.

If a product of the general formula (I) in which $R^o$ is a hydrogen atom is to be obtained, the subsequent removal of the protective radical $R^o$ is carried out by the usual methods, in particular by the methods described by T. W. Greene, by A. Wiley or by McOmie in the abovementioned references.

The perhydroisoindolone derivative of the general formula (III) in which R''' is a hydrogen atom, of the (3aRS, 7aRS) form, can be prepared by the method described in European Patent Application EP 430 771. The (3aS,7aS) stereoisomer is separated off by a method analogous to those described in this application and by the method described below in the examples. The perhydroisoindolone derivative of the general formula (III) in which R''' is a hydroxyl radical which has been protected beforehand can also be prepared by a method analogous to this method, or as described below in the examples.

In general, if a product of the general formula (I) of the (3aS,7aS) form is to be obtained, the separation of the isomeric forms is preferably carried out with the derivative of the general formula (III) or with another intermediate carrying an oxo radical in position 4. Nevertheless, it may also be carried out with the derivative of the general formula (I). The separation is carried out by any known method which is compatible with the molecule.

By way of example, the separation can be carried out by preparation of an optically active salt, by the action of L(+)- or D(−)-mandelic acid or of dibenzoyltartaric acid and then separation of isomers by crystallisation. The desired isomer is liberated from its salt in a basic medium.

The new isoindole derivatives of the general formula (I) are of particular interest as intermediates for the preparation of products of the general formula:

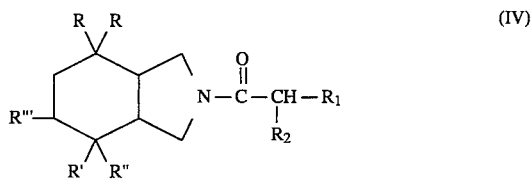

in which R, R', R'' and R''' are as defined above and the symbol $R_1$ represents a phenyl radical which is optionally substituted by one or more halogen atoms, hydroxyl radicals, alkyl radicals, which may be optionally substituted (by halogen atoms or amino, alkylamino or dialkylamino radicals), alkyloxy radicals or alkylthio radicals, which may be optionally substituted [by hydroxyl radicals, amino radicals, alkylamino radicals or dialkylamino radicals which are optionally substituted (by phenyl radicals, hydroxyl radicals or amino radicals), or dialkylamino radicals, the alkyl parts of which, together with the nitrogen atom to which they are attached, form a heterocyclic ring which has 5 to 6 chain members and can contain another hetero atom chosen from oxygen, sulphur and nitrogen, optionally substituted by an alkyl radical, hydroxyl radical or hydroxyalkyl radical)], or substituted by amino radicals, alkylamino radicals, dialkylamino radicals, the alkyl parts of which can form, together with the nitrogen atom to which they are attached, a heterocyclic ring as defined above, or represent a cyclohexadienyl radical, naphthyl radical or mono- or polycyclic, saturated or unsaturated heterocyclic radical containing 5 to 9 carbon atoms and one or more hetero atoms chosen from oxygen, nitrogen and sulphur, and optionally substituted by a halogen atom or by an alkyl or alkyloxy radical, and the symbol $R_2$ represents a hydrogen or halogen atom or a hydroxyl, alkyl, aminoalkyl, alkylaminoalkyl, dialkylaminoalkyl, alkyloxy, alkylthio, acyloxy, carboxyl, alkyloxycarbonyl, dialkylaminoalkyloxycarbonyl, benzyloxycarbonyl, amino or acylamino radical, in the racemic form, in its stereoisomeric forms having the structure:

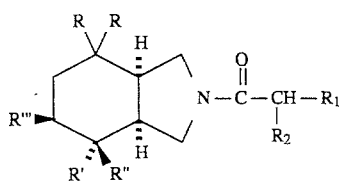

or in its (R) or (S) forms on the chain —CHR₁R₂, or in the form of a mixture of several of these forms, and of their salts, it being understood that the alkyl or acyl radicals mentioned above contain (unless specifically stated otherwise) 1 to 4 carbon atoms in a straight or branched chain.

These perhydroisoindole derivatives are of particular interest as antagonists of substance P.

In the general formula (IV), if $R_1$ contains a halogen atom, this may be chosen from chlorine, bromine, fluorine and iodine.

In the general formula (IV), if $R_1$ represents a mono- or polycyclic, saturated or unsaturated heterocyclic radical, this may be chosen from, by way of example, thienyl, furyl, pyridyl, dithiinyl, indolyl, isoindolyl, benzothienyl, thiazolyl, isothiazolyl, oxazolyl, imidazolyl, pyrrolyl, triazolyl, thiadiazolyl, quinolyl, isoquinolyl and naphthyridinyl.

In the general formula (IV), if $R_1$ represents phenyl which is substituted by a chain carrying a heterocyclic radical, the latter may be chosen from pyrrolidinyl, morpholino, piperidinyl, tetrahydropyridinyl, piperazinyl and thiomorpholino.

Moreover, if the symbol $R_2$ is other than the hydrogen atom, the substituted chain on the isoindole has a chiral centre and it is understood that the stereoisomeric forms and their mixtures also fall under the general formula (IV).

The perhydroisoindole derivatives of the general formula (IV) can be prepared from products according to the invention in the following manner: the acid of the general formula:

or a reactive derivative of this acid, in which $R_1$ and $R_2$ are as defined above, is allowed to act on an isoindole derivative of the general formula (I) in which $R^o$ is a hydrogen atom, and, where appropriate, the product obtained in which R" is a hydroxyl radical and R'" is a hydrogen atom is converted into a product in which R" is a fluorine atom and R'" is a hydrogen atom or into a product in which R" and R'" together form a bond.

It is understood that the amino, alkylamino or carboxyl radicals contained in $R_1$ and/or $R_2$ are preferably protected beforehand. Protection is carried out by any compatible grouping, introduction and removal of which do not affect the remainder of the molecule. In particular, the reaction is carried out by the methods described by T. W. Greene, Protective Groups in Organic Synthesis, A. Wiley—Interscience Publication (1981), or by McOmie, Protective Groups in Organic Chemistry, Plenum Press (1973).

By way of example, amino or alkylamino groupings can be protected by methoxycarbonyl, ethoxycarbonyl, t-butoxycarbonyl, allyloxycarbonyl, vinyloxycarbonyl, trichloroethoxycarbonyl, trichloroacetyl, trifluoroacetyl, chloroacetyl, trityl, benzhydryl, benzyl, allyl, formyl, acetyl or benzyloxycarbonyl radicals or substituted derivatives of benzyloxycarbonyl radicals;

the acid groupings can be protected by methyl, ethyl, t-butyl, benzyl, substituted benzyl or benzhydryl radicals.

Furthermore, if $R_2$ represents a hydroxyl radical, this radical is preferably protected beforehand. The protection is carried out, for example, by an acetyl, trialkylsilyl or benzyl radical, in the form of a carbonate by a radical —COORa, in which Ra is an alkyl or benzyl radical, or in the form of the ketone.

If condensation of a reactive derivative of the acid of the general formula (V) is carried out, the reaction is advantageously carried out by means of the acid chloride, the anhydride, a mixed anhydride or a reactive ester in which the remainder of the ester is a succinimido, optionally substituted 1-benzotriazolyl, 4-nitrophenyl, 2,4-dinitrophenyl, pentachlorophenyl or phthalimido radical.

The reaction is in general carried out at a temperature between −40° and +40° C. in an organic solvent, such as a chlorinated solvent (methylene chloride, dichloroethane or chloroform, for example), a hydrocarbon (toluene, for example), an ether (tetrahydrofuran or dioxane, for example), an ester (ethyl acetate, for example), an amide (dimethylacetamide or dimethylformamide, for example) or a ketone (acetone, for example), or in a mixture of these solvents, in the presence of an acid acceptor, such as an organic nitrogen base, such as, for example, pyridine, dimethylaminopyridine, N-methylmorpholine or a trialkylamine (in particular triethylamine), or such as an epoxide (propylene oxide, for example). It is also possible to carry out the reaction in the presence of a condensing agent, such as carbodiimide [for example dicyclohexylcarbodiimide or 1-(3-dimethylaminopropyl)- 3-ethyl-carbodiimide], N,N'-carbonyldiimidazole or 2-ethoxy-1-ethoxycarbonyl-1,2-dihydroquinoline, or in an aqueous/organic medium, in the presence of an alkaline condensing agent, such as sodium bicarbonate.

In the alternative case where a perhydroisoindole derivative of the general formula (IV) in which R" is a hydroxyl radical and R'" is a hydrogen atom has been obtained and where a perhydroisoindole derivative in which R" is a fluorine atom and R'" is a hydrogen atom is required, the reaction is carried out by fluorination of the derivative obtained above.

The fluorination is carried out under the conditions described above for fluorination of a derivative of the general formula (I) in which R" is hydroxyl, at a temperature of between −30° and +30° C.

In the alternative case where a perhydroisoindole derivative of the general formula (IV) in which R" is a hydroxyl radical and R'" is a hydrogen atom has been obtained and where a perhydroisoindole derivative in which R" and R'" together form a bond is required, the reaction is carried out by dehydration of the derivative obtained above.

The reaction is carried out under the conditions described above for preparation of derivatives of the general formula (I) in which R" and R'" together form a bond, starting from the corresponding perhydroisoindole derivative in which R" is a hydroxyl radical and R'" is a hydrogen atom.

The acids of the general formula (V) can be prepared by the methods described below in the examples, by the methods described in Patent Application EP 429 366 or by a method analogous to these methods.

The new isoindole derivatives of the general formula (I) or the derivatives of the general formula (IV) can be purified, if appropriate, by physical methods, such as crystallisation or chromatography.

If appropriate, the new derivatives of the general formula (I) in which $R^o$ is a hydrogen atom or the products of the general formula (IV) in which the symbols $R_1$ and/or $R_2$ contain amino or alkylamino substituents can be converted into acid addition salts. Examples of acid addition salts which may be mentioned are the salts formed with mineral acids (hydrochlorides, hydrobromides, sulphates, nitrates or phosphates) or with organic acids (succinates, fumarates, tartrates, acetates, propionates, maleates, citrates, methanesulphonates, p-toluenesulphonates or isethionates, or with substitution derivatives of these compounds).

Products of the general formula (I) which are of particular interest are those in which: the symbols R are identical and represent phenyl radicals, the symbol R' represents a phenyl radical which is optionally substituted in position 2 by an alkyl or alkyloxy radical containing 1 or 2 carbon atoms, the symbol R" represents a fluorine atom or a hydroxyl radical and the symbol R''' represents a hydrogen atom, or the symbols R" and R''' represent hydroxyl radicals, or the symbol R" forms a bond with R''', and the symbol $R^o$ represents a hydrogen atom or represents a benzyl or t-butoxycarbonyl radical.

Among these products, those which are more particularly of interest are:

7,7-diphenyl-4-(2-methoxyphenyl)-2-tert-butoxycarbonyl-perhydroisoindol-4-ol;
7,7-diphenyl-4-(2-methoxyphenyl)-perhydroisoindol-4ol;
7,7-diphenyl-4-(2-methoxyphenyl)-2-tert-butoxycarbonyl-perhydroisoindole-4,5-diol;
7,7-diphenyl-4-(2-methoxyphenyl)-perhydroisoindole-4,5-diol; and
2-benzyl-7,7-diphenyl-4-(2-methoxyphenyl)-perhydroidoindole-4,5-diol.

The isoindole derivatives of the general formula (IV) which antagonise the effects of substance P can be used in the fields of analgesia, inflammation asthma or, allergies, on the central nervous system, on the cardiovascular system, as an antispasmodic, or on the immune system, as well as in the field of stimulation of lachrymal secretions.

In fact, the products of the general formula (IV) show an affinity for substance Preceptors in doses of between 10 and 1000 nM by the adapted techniques of D. G. Payan et al., J. of immunology, 133 (6), 3260–5 (1984): Stereospecific receptors for substance P on cultured human IM-9 lymphoblasts and McPherson et al., J. Pharmacol. Meth., 14, 213 (1985): Analysis of radioligand binding experiments.

It has furthermore been demonstrated that the effect is an antagonistic effect on substance P by means of various products. In the technique described by S. Rosell et al., Substance P, Ed. by U. S. Von Euler and B. Pernow, Raven Press, New York (1977), pages 83 to 88, the products studied show antagonism of contractions of the guinea-pig ileum induced by substance P or contractions of the guinea-pig ileum induced by septide at concentrations of 6 to 1000 nM.

Substance P is known to be involved in a certain number of pathological areas:

Agonists and antagonists of substance P, A. S. Dutta Drugs of the future, 12 (8), 782 (1987);

Substance P and pain: an updating, J. L. Henry, TINS, 3 (4), 97 (1980);

Substance P in inflammatory reactions and pain, S. Rosell, Actual. Chim. Ther., 12e`me série, 249 (1985)

Effects of Neuropeptides on Production of Inflammatory Cytokines by Human Monocytes, M. Lotz et al., Science, 241, 1218 (1988).

Neuropeptides and the pathogenesis of allergy, Allergy, 42, 1 to 11 (1987);

Substance P in Human Essential Hypertension, J. Cardiovascular Pharmacology, 10 (suppl. 12), 5172 (1987).

Study of certain isoindole derivatives of the general formula (IV) by the technique of A. Saria et al,, Arch. Pharmacol., 324, 212–218 (1983) adapted for the guinea-pig has demonstrated an inhibitory effect on the increase in capillary permeability caused by septide (agonist of substance P), which is evidence of an antiinflammatory activity:

| Product studied | $ED_{50}$ |
| --- | --- |
| Use Example 1 | 0.04 mg/kg i.v. |
|  | 3.5 mg/kg p.o. |

Injection of substance P into the animal causes hypotension. The products studied by the technique of C. A. Maggi et al., J. Auton. Pharmac., 7, 11–32 (1987) show an antagonistic effect with respect to this hypotension in the guinea-pig. The $ED_{50}$, the dose which reduces by 50% the hypotension induced by an i.v. injection of 250 ng/kg of substance P, is determined.

| Product of the general formula (I) | $ED_{50}$ mg/kg i.v. |
| --- | --- |
| Use Example 1 | 0.15 |

Injection of substance P causes a bronchospasm in the animal. The bronchoconstriction induced in vivo in the guinea-pig by injection of substance P or of a selective agonist of substance P: [$Pro^9$] substance P is studied by the technique of H. Konzett and R. Rosseler, Archiv. Exp. Path. Pharmak., 195, 71–74 (1940). This bronchoconstriction is inhibited by injection of a product of the general formula (IV), which is evidence of an antiasthmatic activity. The $ED_{50}$, the dose which reduces by 50 % the bronospasm induced by 3 µg/kg i.v. of [$Pro^9$] substance P, is determined. In this technique, the $ED_{50}$ of the product of Use Example 1 is 0.7 mg/kg i.v.

Furthermore, the isoindole derivatives of the general formula (IV) show no toxicity and are found to be atoxic in the mouse when administered intravenously in a dose of of 10 mg/kg or subcutaneously in a dose of 40 mg/kg subcutaneously.

EXAMPLES

The following examples are given non-limitatively and illustrate the present invention.

In the examples which follow, it is understood that, unless otherwise stated, the proton NMR spectra were recorded at 250 MHz in dimethyl sulphoxide; the chemical shifts are expressed in ppm.

Example 1

A suspension of 2-methoxyphenylmagnesium bromide (prepared from 75.3 g of 2-bromoanisole and 9.8 g of magnesium) in 100 cm$^3$ of dry tetrahydrofuran are added dropwise, with stirring, to a suspension of 20 g of (3aS, 7aS)-7,7-diphenyl-2-tert-butoxycarbonyl-perhydroisoindol-4-one and 31.6 g of anhydrous cerium chloride in 250 cm$^3$ of dry tetrahydrofuran at room temperature. The reaction mixture is stirred at room temperature for 24 hours, treated with 400 cm³ of a saturated aqueous solution of ammonium chloride, diluted with 200 cm³ of ethyl acetate, washed with 300 cm³ of water (twice) and then with 300 cm³ of a saturated aqueous solution of sodium chloride, dried over magnesium sulphate, filtered and concentrated to dryness under reduced pressure (2.7 kPa). The residue is chromatographed over a Merck silica gel column (particle size 0.04–0.06 mm, diameter 5.8 cm, height 26.5 cm) by eluting under a pressure of 0.5 bar of nitrogen with a mixture of cyclohexane and ethyl acetate (80/20 by volume) and collecting fractions of 100 cm³. Fractions 9 to 29 are combined and concentrated to dryness under reduced pressure (2.7 kPa). 17.82 g of (3aS,4S,7aS)-7,7-diphenyl-4-(2methoxphenyl)-2 -tert -butoxycarbonyl-perhydroisoindol-4ol are obtained in the form of a white foam.

Proton NMR spectrum (DMSO $d_6$): 1.36 (s, 9H, —C(CH$_3$)$_3$); 1.54 (dmt, J=14, 1H, equatorial H of —C$_2$— in 5); 2.3 (dmt, J=14, 1H, equatorial H of —CH$_2$—in 6); 2.34 (td, J=14 and 2.5, 1H, axial H of —CH$_2$—in 5); 3.07 (td, J=14 and 2.5, axial H of —CH$_2$—in 6); 3.49 (s, 3H, —OCl$_3$); 2.6 to 3.6 (mt, other —CH$_2$—and —CH); 6.85 to 7.7 (mt, 14H, aromatic).

100 cm³ of a 5.2N solution of hydrogen chloride in dioxane are added to a solution of 7.63 g of (3aS, 4S, 7aS) -7,7-diphenyl-4-(2-methoxyphenyl) -2-tert-butoxycarbonyl-perhydroisoindol- 4-ol in 66 cm³ of dioxane at room temperature. The reaction mixture is stirred at this temperature for 1 hour and then concentrated to dryness under reduced pressure (2.7 kPa). The residue is washed with acetonitrile, filtered off and then dried. 4.88 g of (3aS,4S,7aS)-7,7- diphenyl-4-(2 -methoxyphenyl )-perhydroisoindol-4-ol hydrochloride are obtained in the form of white crystals which melt at 271° C. (Maquenne block).

(3aS, 7aS)-7,7-Diphenyl-tert-2 -butoxycarbonyl-perhydroisoindol-4-one can be obtained in the following manner:

34.3 cm³ of triethylamine, 58.6 g of di-tert-butyl dicarbonate and 2.98 g of 4-dimethylaminopyridine are added, with stirring, to a suspension of 80 g of (3aS, 7aS) -7,7-diphenyl-perhydroisoindol-4-one hydrochloride in 400 cm³ of dry methylene chloride at room temperature. The reaction mixture is stirred at room temperature for 24 hours, washed with 100 cm³ of an aqueous solution of citric acid, then with 100 cm³ of an aqueous solution of sodium bicarbonate and then with 100 cm³ of an aqueous saturated solution of sodium chloride, dried over magnesium sulphate and concentrated to dryness under reduced pressure (2.7 kPa). 106.5 g of (3aS,7aS)-7,7-diphenyl-tert-2-butoxycarbonyl-perhydroisoindol-4-one are obtained in the form of an orange foam.

Proton NMR spectrum (DMSO $d_6$): 1.4 (s, 9H, —C(CH$_3$)$_3$) 2.11 (td, J=15 and 7.5, 1H, axial H of —CH$_2$— in 5); 2.3 (dr, J=15 and 3.5, 1H, equatorial H of —CH$_2$— in 5 ); 2.75 to 2.9 (mr, 4H, —CH$_2$— in 6 and —CH$_2$— in 1); 3.26 (dd, J=7.5 and 7, 1H, —CH in 3a); 3.35 (dd, J=11 and 7, 1H, 1H of —CH$_2$— in 3); 3.97 (mr, 1H, —CH in 7a); 4.1 (d, j=11, 1H, the other H of —CH$_2$— in 3 ); 7.1 to 7.7 (mr, 10H, aromatic).

(3aS, 7aS)-7,7-diphenyl-perhydroisoindol-4-one hydrochloride can be obtained in the following manner:

50 cm³ of aqueous 4N sodium hydroxide are slowly added to a suspension of 20 g of (3aRS,7aRS)-7,7-diphenyl-perhydroisoindol-4-one hydrochloride in 250 cm³ of ethyl acetate, while stirring; stirring is continued until the starting substance has disappeared. The organic solution is washed with 100 cm³ of distilled water and with 100 cm³ of a saturated solution of sodium chloride, dried over magnesium sulphate and filtered. A solution of 9.3 g of D-(–)mandelic acid in 50 cm³ of ethyl acetate is added to the solution thus obtained, while stirring. The crystals formed are filtered off, drained, washed with 50 cm³ of ethyl acetate (twice) and dried. The crystals are taken up in a solution of 220 cm³ of acetonitrile and 60 cm³ of distilled water and the mixture is refluxed for 15 minutes, while stirring; the crystals formed are filtered off and recrystallised in a mixture of 100 cm³ of acetonitrile and 35 cm³ of distilled water. 6.4 g of (3aS, 7aS)-7,7-diphenyl-perhydroisoindol-4-one D-mandelate are obtained.

50 cm³ of aqueous 1N sodium hydroxide are added to 6.4 g of (3aS,7aS)-7,7-diphenyl-perhydroisoindol-4-one D-mandelate dissolved in 100 cm³ of ethyl acetate; the reaction mixture is stirred at room temperature until the starting substance has disappeared; the organic solution is washed with 50 cm³ of distilled water and with 50 cm³ of an aqueous saturated solution of sodium chloride, dried over magnesium sulphate and filtered; it is acidified by addition of 2 cm³ of a 9N solution of hydrochloric acid in ethanol, while stirring; the crystals obtained are filtered off, washed with ethyl acetate and then with isopropyl ether and dried. 4.24 g of (3aS,7aS)-7,7-diphenyl-perhydroisoindol-4-one hydrochloride are obtained in the form of white crystals which melt at 270° C. with decomposition.

(S)-2-(2-Methoxyphenyl)-propionic acid can be prepared by a method analogous to those described by D. A Evans et al., Tetrahedron, 44, 5525, (1988), in accordance with the following operating method:

1.52 g of lithium hydroxide are added to a solution, cooled to +5° C., of 4.1 g of (4S,5S)-4-methyl-5-phenyl-3-[2-(2-methoxyphenyl)-(S)-propionyl]-oxazolidin-2-one in 60 cm³ of tetrahydrofuran and 30 cm³ of water. The reaction mixture is stirred at this temperature for 3 hours and, after returning to room temperature, ethyl acetate is added, the mixture is decanted, the aqueous phase is acidified with an aqueous 1N solution of hydrochloric acid and extracted with ethyl acetate, and the organic phase is dried over magnesium sulphate and concentrated to dryness under reduced pressure (2.7 kPa). The solid obtained is recrystallised from hexane, filtered off and dried. 0.4 g of (S)-2-(2-methoxyphenyl)-propionic acid is obtained in the form of white crystals which melt at 102° C. $[\alpha]_D^{20}$=+84.6° (c=1; CHCl$_3$).

(4S,5S)-4-Methyl-5-phenyl-3-[2-(2-methoxyphenyl)-(S)-propionyl]-oxazolidin-2-one can be obtained in the following manner:

19.1 g of sodium 1,1,1,3,3,3-hexamethyldisilazanate are added to a solution, cooled to –50° C., of 10 g of (4S,5S)-4-methyl-5-phenyl-3-[(2-methoxyphenyl)-acetyl] -oxazolidin-2-one in 150 cm³ of tetrahydrofuran, the mixture is stirred at this temperature for 45 minutes and 7.72 cm³ of methyl iodide are then added. The reaction mixture is subsequently stirred at room temperature for 15 hours and then diluted with ethyl acetate, washed with 50 cm³ of water and then with 50 cm³ of an aqueous saturated solution of sodium chloride, dried over magnesium sulphate and concentrated to dryness under reduced pressure (2.7 kPa). The residue obtained is crystallised in isopropyl ether, filtered off and dried. 4.2 g of (4S,5S)-4-methyl-5-phenyl-3-[2-(2-methoxyphenyl)-(S)-propionyl] -oxazolidin-2-one are obtained in the form of a white solid.

(4S,5S)-4-Methyl-5-phenyl-3-(2-methoxyphenylacetyl)-oxazolidin-2-one can be obtained in the following manner:

9.38 g of 2-methoxyphenylacetic acid are added to a suspension of 1.89 g of sodium hydride (80% strength dispersion in vaseline) in 200 cm³ of dry tetrahydrofuran at room temperature. This suspension is cooled to −30° C., 7.77 cm³ of pivaloyl chloride are added and, finally, a solution, cooled to −78° C., obtained by adding 35.27 cm³ of a 1.6M solution of butyllithium in hexane to a solution, cooled to −78° C., of 10 g of (4S,5S)-4-methyl-5-phenyl-oxazolidin-2-one in 200 cm³ of dry tetrahydrofuran is added. The reaction mixture is stirred at −30° C. for 45 minutes and, after returning to room temperature, 200 cm³ of an aqueous saturated solution of ammonium chloride and then 500 cm³ of ethyl acetate are added; after decanting, the organic phase is washed twice with 100 cm³ of water and then twice with 100 cm³ of an aqueous saturated solution of sodium chloride, dried over magnesium sulphate and concentrated to dryness under reduced pressure (2.7 kPa). The residue is chromatographed over a silica gel column (particle size 0.04–0.06 mm, diameter 4.8 cm, height 36 cm) by eluting under a pressure of 0.6 bar of nitrogen with a mixture of cyclohexane and ethyl acetate (85/15 and then 80/20 by volume) and collecting fractions of 50 cm³. Fractions 14 to 31 are combined and concentrated to dryness under reduced pressure (2.7 kPa). 13.6 g of (4S,5S)-4-methyl-5-phenyl-3-(2-methoxyphenylacetyl)-oxazolidin-2-one are obtained in the form of a yellow oil.

Example 2

By working in accordance with the operating method of Example 1, starting from 3 g of (3aS,7aS)7,7-diphenyl-2-tert-butoxycarbonyl-perhydroisoindol-4one and a suspension of 2-methylphenylmagnesiumbromide bromide (prepared from 4.6 cm³ of 2-bromotoluene and 0.93 g of magnesium in 15 cm³ of anhydrous tetrahydrofuran), 1.5 g of (3aS,4S,7aS)-7,7-diphenyl-4-(2-methylphenyl)-2-tert-butoxycarbonyl-perhydroisoindol-4-ol are obtained in the form of an oil which is used as such in the following test.

(3aS,4S,7aS)-7,7-diphenyl-4-(2-methylphenyl)-perhydroisoindol-4-ol hydrochloride can be prepared in the following manner:

By working in accordance with Example 1, starting from 1.2 g of (3aS,4S,7aS)-7,7-diphenyl-4-(2 -methylphenyl)-2-tert-butoxycarbonyl-perhydroisoindol-4-ol, 0.68 g of (3aS, 4S,7aS)-7,7-diphenyl-4-(2 -methylphenyl)-perhydroisoindol-4-ol hydrochloride, are obtained.

Infrared spectrum (KBr), characteristic bands (cm⁻¹): 3325, 3100–3000, 3000–2850, 3000–2300, 1600, 1585, 1560, 1495, 1445, 750, 700.

EXAMPLE 3

By working in accordance with the operating method of Example 1, starting from 2.75 g of (3aRS,7aRS)-7,7-diphenyl-2-tert-butoxycarbonylperhydroisoindol-4one, 1.73 g of anhydrous cerium chloride and a suspension of 2-methoxyphenylmagnesium bromide (obtained from 6.57 g of 2-bromoanisole and 0.84 g of magnesium), 2.72 g of (3aRS,4RS,7aRS)-7,7-diphenyl-4-(2 methoxyphenyl )-2-tert-butoxycarbonylperhydroisoindol-4-ol are obtained in the form of a white foam.

Proton NMR spectrum (DMSO d₆): at room temperature, a mixture of rotamers is found: 1.3 and 1.35 (mr, 1H, 1H of —CH₂— in 5); 2.15 to 2.4 (mr, 2H, the other H of —CH₂— in 5 and 1H of —CH₂— in 6); 2.5 to 3.6 (mt, —CH₂— and —CH<); 3.35 and 3.39 (2s, 3H, —OCH₃); 4.68 and 4.72 (2s, 1H, —OH); 6.8 to 7.7 (mt, 14H aromatic).

By working in accordance with the operating method of Example 1, starting from 2.7 g of (3aRS, 4RS, 7aRS)-7,7-diphenyl-4-(2-methoxyphenyl)-2 -tert-butoxycarbonyl-perhydroisoindol-4-ol, 1.77 g of (3aRS, 4RS, 7aRS) -7,7-diphenyl-4-(2-methoxyphenyl)perhydroisoindol-4-ol hydrochloride are obtained in the form of a white solid.

Proton NMR spectrum (DMSO d₆): 1.55 (d broad, J=14, 1H, equatorial H of —CH₂— in 5); 2.34 (td, J=14 and 2.5, 1H, axial H of —CH₂— in 5); 2.37 (d broad, J=14, 1H, equatorial H of —CH₂— in 6); 2.52 (mt, 1H of —CH₂— in 1); 2.93 (td, J=14 and 2.5; 1H, axial H of —CH₂— in 6); 3 to 3.3 (mt, 3H, —CH₂— in 3 and the other H of —CH₂— in 1); 3.42 (s, 3H, —OCH₃—); 3.4 to 3.7 (mt, 2H, —CH< in 3a and 7a); 5.3 (mf extended, 1H, —OH); 6.8 to 7.7 (mt, 14H, aromatic).

(3aRS, 7aRS)-7,7-diphenyl-2-tert-butoxycarbonyl-perhydroisoindol-4-one can be prepared in the following manner:

4.3 cm³ of triethylamine, 7.4 g of di-tert-butyl dicarbonate and then 0.37 g of 4-dimethylaminopyridine are added to a suspension of 10 g of (3aRs, 7 aRS )-7,7-diphenyl-perhydroisoindol-4-one hydrochloride in 50 cm³ of dry methylene chloride at room temperature, while stirring. The reaction mixture is stirred at room temperature for 24 hours, washed with 150 cm³ of an aqueous solution of citric acid, subsequently with 100 cm³ of an aqueous solution of sodium bicarbonate and then with 100 cm³ of an aqueous saturated solution of sodium chloride, dried over magnesium sulphate and concentrated to dryness under reduced pressure (2.7 kPa). 11 g of (3aRS,7aRS)-7,7-diphenyl-2 -tert-butoxycarbonyl-perhydroisoindol-4 -one are obtained in the form of a cream foam.

Proton NMR spectrum (DMSO d6): 1.38 (s, 9H, —C(CH₃)₃); 2.08 (td, J=14 and 6, 1H, axial H of —CH₂— in 5); 2.28 (dmt, 1H, equatorial H of —CH₂— in 5); 2.7 to 2.85 (mt, 4H, —CH₂— in 1 and —CH₂— in 6); 3.27 (mt, 2H, —CH< in 3a and 1H of —CH₂— in 3); 3.9 to 4.05 (mt, 2H, —CH< in 7a and the other H of —CH₂— in 3); 7.1 to 7.7 (mt, 10H aromatic).

Example 4

A suspension of 10.78 g of phenylmagnesium bromide in 65 cm³ of diethyl ether is added dropwise to a solution of 11.66 g of (3aS,7aS)-7,7-diphenyl-2-tert-butoxycarbonyl-perhydroisoindol-4-one in 70 cm³ of dry tetrahydrofuran at room temperature, while stirring. The reaction mixture is stirred at room temperature for 24 hours, refluxed for 5 hours and then treated with 250 cm³ of an aqueous saturated solution of ammonium chloride, diluted with 200 cm³ of ethyl acetate, washed with 200 cm³ of water (twice) and then with 200 cm³ of an aqueous saturated solution of sodium chloride, dried over magnesium sulphate, filtered and concentrated to dryness under reduced pressure (2.7 kPa). The residue is chromatographed over a Merck silica gel column (particle size 0.04–0.06 mm, diameter 5.3 cm, height 31.5 cm), by eluting under a pressure of 0.5 bar of nitrogen with a mixture of cyclohexane and ethyl acetate (90/10 by volume) and collecting fractions of 100 cm³. Fractions 23 to 48 are combined and concentrated to dryness under reduced pressure (2.7 kPa). 5.75 g of (3aS,4S,7aS)-4,7,7-triphenyl-2 -tert-butoxycarbonyl-perhydroisoindol-4-ol are obtained in the form of a pale yellow foam.

Proton NMR spectrum (DMSO d₆): 1.37 (s, 9H, —C(CH₃)₃); 1.65 (mt, 2H, —CH₂ in 5); 2.28 (d broad, J=14, 1H, equatorial H of —CH₂— in 6); 2.65 (t, J=9, 1H of —CH₂— in 1); 2.85 (mt, 1H, —CH< in 3a); 3.05 (td, J=14 and 3.5; 1H, axial H of —CH₂— in 6); 3.25 (mt, 2H, the other H of —CH₂— in 1 and 1H of —CH₂— in 3); 3.4 (d, J=11, 1H, the other Hof —CH₂— in 3); 3.5 (mt, 1H, —CH< in 7a); 4.4 (s, 1H, OH); 7.1 to 7.6 (mt, 15H aromatic).

Infrared spectrum (KBr), characteristic bands (cm$^1$): 3425, 3100–3000, 3000–2850, 1680, 1600, 1580, 1495, 1475, 1410, 1365, 1170, 750, 700.

A solution of 6.3N hydrochloric acid in 115 cm$^3$ of dioxane is added to a solution of 6.8 g of (3aS, 4S, 7aS)-4,7,7-triphenyl-2-tert-butoxycarbonyl-perhydroisoindol-4-ol in 60 cm$^3$ of dioxane at room temperature. The reaction mixture is stirred at this temperature for 2 hour and then concentrated to dryness under reduced pressure (2.7 kPa). The residue is washed with acetonitrile, filtered off and then dried. 4 g of (3aS, 4S, 7aS)-4,7,7- triphenyl-perhydroisoindol-4-ol hydrochloride are obtained in the form of a white foam.

Proton NMR spectrum (DMSO d$_6$): 1.51 (td, J=14, 1H, axial H of —CH$_2$— in 5); 1.72 (d broad J=14, 1H, equatorial H of —CH$_2$— in 5); 2.34 (d broad, J=14, 1H, equatorial H of —CH$_2$— in 6); 2.42 (td, J=10, 1H of —CH$_2$— in 1); 2.87 (td, J=14, 1H, axial H of —CH$_2$— in 6); 2.94 (mt, 1H, —CH< in 3a); 3.05 to 3.25 (mt, 3H, the other H of —CH$_2$— in 1 and the —CH$_2$— in 3); 3.57 (mt, 1H, —CH< in 7a); 5.67 (mf, 1H, OH); 7.1 to 7.6 (mt, 15H aromatic); 8.9 (2mf 1H each NH$_2^+$)

Infrared spectrum (KBr), characteristic bands (cm$^1$): 3500–3250, 3100–3000, 3000–2825, 2800–2250, 1600, 1580, 1495, 1445, 1075, 750, 700.

Example 5

A suspension of 30.9 g of 2-methoxyphenyl-magnesium bromide in 170 cm$^3$ of dry tetrahydrofuran is added dropwise to a suspension of 26.4 g of (3aRS,5RS,7aRS)-5-acetoxy-7,7-diphenyl-4-(2-methoxyphenyl)-2 -tert-butoxycarbonyl-perhydroisoindol-4-one and 43.3 g of anhydrous cerium chloride in 265 cm$^3$ of dry tetrahydrofuran at room temperature, while stirring. The reaction mixture is stirred at room temperature for 24 hours, treated with 400 cm$^3$ of an aqueous saturated solution of ammonium chloride, taken up in 1000 cm$^3$ of ethyl acetate and then filtered over celite. The organic phase is decanted, dried over magnesium sulphate, filtered and concentrated to dryness under reduced pressure (2.7 kPa). The residue is chromatographed over a Merck silica gel column (particle size 0.04–0.06 mm, diameter 7 cm, height 55 cm) by eluting under a pressure of 0.5 bar of nitrogen with a mixture of cyclohexane and ethyl acetate (70/10 by volume) and collecting fractions of 250 cm$^3$. Fractions 10 to 19 are combined and concentrated to dryness under reduced pressure (2.7 kPa). 18 g of (3aRS,4RS,5RS,7aRS)-7,7-diphenyl-4-(2-methoxyphenyl)-2-tert-butoxycarbonyl-Perhydroisoindole-4,5-diol are obtained in the form of white crystals which melt at 229° C.

A solution of 6N hydrochloric acid in 25 cm$^3$ of dioxane is added to a solution of 5.15 g of (3aRs,4RS,5RS,7aRS)-7,7-diphenyl-4-(2-methoxyphenyl)-2 -tert-butoxycarbonyl-perhydroisoindole-4,5-diol in 25 cm$^3$ of dioxane at room temperature. The reaction mixture is stirred at this temperature for 1 hour and then concentrated to dryness under reduced pressure (2.7 kPa). The residue is washed with 20 cm$^3$ of acetonitrile, filtered off and dried. 4.5 g of (3aRS, 4RS,5RS,7aRS)-7,7-diphenyl-4-(2-methoxyphenyl)-perhydroisoindole-4,5-diol hydrochloride are obtained in the form of white crystals which melt at a temperature above 300° C.

(3aRS,5RS,7aRS)-5-Acetoxy-7,7-diphenyl-2-tert-butoxycarbonyl-perhydroisoindol-4-one can be prepared in the following manner:

46.9 cm$^3$ of triethylamine, 11.8 g of di-tert-butyl dicarbonate and then 0.3 g of 4-dimethylaminopyridine are added to a suspension of 19 g of (3aRS,5RS,7aRS)-5-acetoxy-7, 7-diphenyl-perhydroisoindol-4-one hydrochloride in 200 cm$^3$ of dry methylene chloride at a temperature of about 5° C., while stirring. The reaction mixture is stirred at room temperature for 24 hours and then washed with an aqueous saturated solution of sodium bicarbonate. The organic phase is decanted, dried over magnesium sulphate, filtered and concentrated to dryness under reduced pressure (2.7 kPa). The residue is crystallised in 120 cm$^3$ of diisopropyl ether. 21 g of (3aRS,5RS,7aRS)-5-acetoxy-7,7-diphenyl-perhydroisoindol-4-one are obtained in the form of white crystals which melt at 213° C.

(3aRS,5RS,7aRS)-5-Acetoxy-7,7-diphenyl-perhydroisoindol-4-one hydrochloride can be prepared in the following manner:

A solution of 5.2N hydrochloric acid in 394 cm$^3$ of dioxane is added to a solution of 51.2 g of (3aRS,SRS, 7aRS)-5-acetoxy-7,7-diphenyl-2-vinyloxy-carbonyl-perhydroisoindolin-4 -one in 118 cm$^3$ of dioxane at room temperature. The reaction mixture is stirred at this temperature for 1 hour and then concentrated to dryness under reduced pressure (2.7 kPa). The residue is recrystallised from 200 cm$^3$ of boiling ethanol. 13.4 g of (3aRS,5RS,7aRS)-5-acetoxy-7,7-diphenyl-pehydroisoindol-4-one hydrochloride are obtained in the form of white crystals which melt at a temperature above 300° C.

(3aRS,5RS,7aRS)-5-Acetoxy-7,7-diphenyl-2-vinyloxycarbonyl-perhydroisoindolin-4-one can be prepared in the following manner:

13.6 cm$^3$ of vinyl chloroformate are added to a solution of 58 g of (3aRS,5RS,7aRS)-5-acetoxy-2-benzyl-7,7 -diphenyl-perhydroisoindolin-4-one in 580 cm$^3$ of dry methylene chloride at room temperature, while stirring. The reaction mixture is kept at the reflux temperature of the solvent for one hour, cooled to room temperature and concentrated to dryness under reduced pressure (2.7 kPa). The residue is crystallised in 400 cm$^3$ of a mixture of diisopropyl ether and petroleum ether (50/50 by volume). 51.4 g of (3aRS,5RS, 7aRS)-5-acetoxy-7,7 -diphenyl-2-vinyloxycarbonyl-perhydroisoindol-4-one are obtained in the form of yellow crystals which melt at 205°–210° C.

(3aRS,5RS,7aRS)-5-Acetoxy-2-benzyl-7,7 -diphenyl-perhydroisoindol-4-one can be prepared in the following manner:

15 drops of trifluoroacetic acid are added to a solution of 86 g of 6-acetoxy-4,4-diphenylcyclohexane-2-one and 96 cm$^3$ of N-butoxymethyl-N-trimethylsilymethyl-benzylamine in 1000 cm$^3$ of methylene chloride. The reaction mixture is stirred at room temperature for 15 hours, 2 g of sodium carbonate are then added and the mixture is concentrated to dryness under reduced pressure (2.7 kPa). The residue is chromatographed over a Merck silica gel column (particle size 0.04–0.06 mm, diameter 7 cm, height 70 cm) by eluting under a pressure of 0.5 bar of nitrogen with a mixture of cyclohexane and ethyl acetate (20/80 by volume) and collecting fractions of 200 cm$^3$. Fractions 6 to 10 are combined and concentrated to dryness under reduced pressure (2.7 kPa). 70 g of (3aRS,5RS,7aRS)-5-acetoxy-2-benzyl-7,7-diphenyl-perhydroisoindol-4-one are obtained in the form of a syrup (melting point below 40° C).

N-Butoxymethyl-N-trimethylsilylmethylbenzylamine can be prepared by the method of Y. TERAO et al., Chem. Pharm. Bull., 33, 2762 (1985).

6-Acetoxy-4,4-diphenyl-cyclohexen-2-one can be prepared by the method described by W. OPPOLZER et al., Helv. Chim. Acta, 59, 2012 (1976).

Example 6

(3aS, 4S, 7aS)-7,7-Diphenyl-4-fluoro-4-(2-methoxyphenyl)-perhydroisoindole hydrochloride can be obtained in the following manner:

A solution of 6.3N hydrochloric acid in 20 cm³ of dioxane is added to a solution of 2.07 g of (3aS,4S,7aS)-7,7-diphenyl-4-fluoro-4-(2-methoxyphenyl)- 2-tert-butoxycarbonyl-perhydroisoindole in 20 cm³ of dioxane at room temperature. The reaction mixture is stirred at this temperature for 3 hours and then concentrated to dryness under reduced pressure (2.7 kPa). The residue is crystallised in 40 cm³ of absolute ethanol and the crystals are filtered off and then dried. 1 g of (3aS,4S,7aS)-7,7-diphenyl-4-fluoro-4-(2-methoxyphenyl)-perhydroisoindole hydrochloride is obtained in the form of white crystals which melt at 270° C.

(3aS,4S,7aS)-7,7-Diphenyl-4-fluoro-4-(2-methoxyphenyl)-2-tert-butoxycarbonyl-perhydroisoindole can be obtained in the following manner:

A solution of 4.3 cm³ of diethylaminosulphur trifluoride in 20 cm³ of dry methylene chloride is added dropwise to a solution, cooled to 0° C., of 6.48 g of (3aS,4S,7aS)-7,7-diphenyl-4-(2-methoxyphenyl)-2-tert-butoxycarbonyl-perhydroisoindol-4-ol in 70 cm³ of dry methylene chloride. The reaction mixture is stirred at this temperature for 3 hours, washed with 100 cm³ of an aqueous saturated solution of sodium bicarbonate and then with 100 cm³ of an aqueous saturated solution of sodium chloride, dried over magnesium sulphate and concentrated to dryness under reduced pressure (2.7 kPa). The residue is chromatographed over a Merck silica gel column (particle size 0.04–0.06 mm, diameter 4.8 cm, height 26 cm) by eluting under a pressure of 0.5 bar of nitrogen with a mixture of cyclohexane and ethyl acetate (95/5 by volume) and collecting fractions of 50 cm³. Fractions 34 to 63 are combined and concentrated to dryness under reduced pressure (2.7 kPa). 2.2 g of (3aS,4S,7aS)-7,7-diphenyl-4-fluoro-4-(2-methoxyphenyl)-2-tert-butoxycarbonyl-perhydroisoindole are obtained in the form of a white foam.

Example 7

(3aS,7aR)-4,4-Diphenyl-7-(2-methoxyphenyl)-2,3,3a,4,5,7a-hexahydroisoindole hydrochloride can be obtained in the following manner:

A solution of 8.56 g of (3aS,4S,7aS)-7,7-diphenyl-4-(2-methoxyphenyl)-2-tert-butoxycarbonyl-perhydroisoindol-4-ol in 53 cm³ of acetic acid and 30 cm³ of 12N hydrochloric acid is heated at 95° C. for 45 minutes, and then cooled to room temperature and concentrated to dryness under reduced pressure (2.7 kPa). The residue is recrystallised from 20 cm³ of acetonitrile. 5.2 g of (3aS,7aR)-4,4-diphenyl-7-(2-methoxyphenyl)- 2,3,3a, 4,5,7a-hexahydroisoindole hydrochloride are obtained in the form of white crystals which melt at a temperature above 300° C., and the product is used in the crude state in the subsequent syntheses.

Example 8

A solution of 22 g of (3aRS,SRS,7aRS)-5-acetoxy-2-benzyl-7,7-diphenyl-perhydroisoindol-4-one in 220 cm³ of tetrahydrofuran is added dropwise to a suspension of 84.4 g of 2-methoxyphenylmagnesium bromide in 1000 cm³ of tetrahydrofuran at room temperature, while stirring. The reaction mixture is stirred at room temperature for 18 hours, treated with 200 cm³ of an aqueous saturated solution of ammonium chloride and taken up in 200 cm³ of ethyl ether and 200 g of ice. The organic phase is decanted, dried over magnesium sulphate, filtered and concentrated to dryness under reduced pressure (2.7 kPa). The residue is crystallised in 250 cm³ of petroleum ether and then recrystallised from 200 cm³ of methanol; the crystals are washed with 200 cm³ of isopropyl ether. 16.4 g of (3aRS, 4RS, 5RS, 7aRS)-2-benzyl-7,7-diphenyl-4-(2-methoxyphenyl)-perhydroisoindole-4,5-diol which melts at 236° C. are obtained.

Example 9

520 cm³ of water and 70 cm³ of aqueous 1N sodium hydroxide are added to 13 g of (3aS,4S,5S,7aS)-7,7-diphenyl-4-(2-methoxyphenyl)-perhydroisoindole-4,5-diol 1,4-ditoluoyl-L-tartrate, dissolved in 260 cm³ of methanol; the reaction mixture is stirred at room temperature until the starting substance has disappeared. The crystals formed are filtered off, drained and dried. 7.6 g of (3aS,4S,5S,7aS)-7,7-diphenyl-4-(2-methoxyphenyl)-perhydroisoindole-4,5-diol which melts at 235° C. are obtained.

(3aS,4S,5S,7aS)-7,7-Diphenyl-4-(2-methoxyphenyl)-perhydroisoindole-4,5-diol 1,4-ditoluoyl-L-tartrate can be prepared in the following manner:

29.2 g of (−)-1,4-ditoluoyl-D-tartaric acid are added to a solution of 30 g of (3aRS,4RS,5RS,7aRS)-7,7-diphenyl-4-(2-methoxyphenyl)-perhydroisoindole-4,5-diol in 500 cm³ of methanol, while stirring. After all the solids have dissolved, the reaction mixture is concentrated to dryness under reduced pressure (2.7 kPa); the foam obtained is crystallised in 500 cm³ of ethyl ether. The crystals obtained are recrystallised in a mixture of ethanol and water (60/40 by volume) at a constant rotary power. 13.3 g of (3aS,4S,5S,7aS)-7,7-diphenyl-4-(2-methoxyphenyl)-perhydroisoindole-4,5-diol 1,4-ditoluoyl-L-tartrate which melts at 240° C. are obtained.

(3aRS,4RS,5RS,7aRS)-7,7-Diphenyl-4-(2-methoxyphenyl-perhydroisoindole-4,5-diol can be prepared in the following manner:

A mixture of 2 g of (3aRS,4RS,5RS,7aRS)-2-benzyl-7,7-diphenyl-4-(2-methoxyphenyl)-perhydroisoindole-4,5-diol and 50 cm³ of ethanol is heated at 65° C., while stirring; 0.65 g of 20% palladium hydroxide-on-charcoal is added and the reaction mixture is then hydrogenated at a temperature of 65° C. and under atmospheric pressure, while stirring. After a reaction time of 1 hour, the theoretical volume of hydrogen has been absorbed; the reaction mixture is filtered and then concentrated to dryness under reduced pressure (2.7 kPa). The residue is crystallised in 10 cm³ of isopropyl ether. 1.45 g of (3aRS,4RS,5RS,7aRS)-7,7-diphenyl-4-(2-methoxyphenyl)-perhydroisoindole-4,5-diol which melts at 230° C. are obtained.

Use Example 1

0,025 g of 1-hydroxybenzotriazole, 0.38 g of (S)-2-(2-methoxyphenyl)-propionic acid and 0.32 cm³ of diisopropylethylamine are added to a suspension of 0.8 g of (3aS, 4S,7aS)-7,7-diphenyl-4-(2 -methoxyphenyl)-perhydroisoindol-4-ol hydrochloride in 60 cm³ of dry methylene chloride, this solution is then cooled to +5° C. and a suspension of 0.43 g of 1-(3-dimethylaminopropyl)-3-ethyl-carbodiimide hydrochloride in 10 cm³ of dry methylene chloride is added rapidly. The reaction mixture is stirred at +5° C. for 2 hours and at room temperature for 2 hours, washed with 20 cm³ of water, subsequently washed with 20 cm³ of an aqueous saturated solution of sodium chloride (twice), dried over magnesium sulphate and concentrated to dryness under reduced pressure (2.7 kPa). The residue is chromatographed over a Merck silica gel column (particle size 0.04–0.06 mm, diameter 2.8 cm, height 20 cm) by eluting under a pressure of 0.5 bar of nitrogen with a mixture of cyclohexane and ethyl acetate (80/20 by volume) and collecting fractions of 25 cm$^3$. Fractions 9 to 15 are combined and then concentrated to dryness under reduced pressure (2.7 kPa). The residue is crystallised in a mixture of acetonitrile and diisopropyl ether. 0.17 g of (3aS,4S,7aS)-7,7-diphenyl-4-(2-methoxyphenyl)-2-[2-(2-methoxyphenyl)-(S)-propionyl]-perhydroisoindol-4-ol is obtained in the form of white crystals which melt at 244° C.

Use Example 2

By working in accordance with the operating method of Use Example 22 below, starting from 0.68 g of (3aS,4S,7aS)-7,7-diphenyl-4-(2-methylphenyl)-perhydroisoindol-4-ol hydrochloride and 0.28 cm$^3$ of phenylacetyl chloride, 0.4 g of (3aS,4S,7aS)-7,7-diphenyl-4-(2-methylphenyl)-2-phenylacetyl-perhydroisoindol-4-ol is obtained in the form of white crystals which melt at 208° C.

Use Example 3

0.35 cm$^3$ of triethylamine and then 0.33 cm$^3$ of phenylacetyl chloride are added to a suspension of 1.1 g of (3aRS,4RS,7aRS)-7,7-diphenyl-4-(2-methoxyphenyl)-perhydroisoindol-4-ol hydrochloride in 25 cm$^3$ of dry methylene chloride at room temperature. The reaction mixture is stirred at this temperature for 24 hours, diluted with 200 cm$^3$ of methylene chloride, washed with 100 cm$^3$ of a saturated solution of sodium bicarbonate, with 100 cm$^3$ of water (twice) and then with an aqueous saturated solution of sodium chloride, dried over magnesium sulphate, filtered and concentrated to dryness under reduced pressure (2.7 kPa). The residue is chromatographed over a Merck silica gel column (particle size 0.04–0.06 mm, diameter 2 cm, height 22 cm) by eluting under a pressure of 0.5 bar of nitrogen with a mixture of cyclohexane and ethyl acetate (55/45 by volume) and collecting fractions of 20 cm$^3$. Fractions 11 to 18 are combined and concentrated to dryness under reduced pressure (2.7 kPa). The residue obtained is crystallised in 70 cm$^3$ of acetonitrile and the crystals are filtered off and dried. 0.5 g of (3aRS,4RS,7aRS)-7,7-diphenyl-4-(2-methoxyphenyl)-2-phenylacetyl-perhydroisoindol-4-ol is obtained in the form of a white solid.

Proton NMR spectrum (DMSO d$_6$): 1.5 (dmt, J=14, 1H, 1 equatorial H of —CH$_2$— in 5); 2.26 (dmt, J=14, 1H, equatorial H of —CH$_2$— in 6); 2.31 (td, J=14 and 3, 1H, axial H of —CH$_2$— in 5); 2.85 (mt, 1H, —CH in 3a); 3.02 (td, J=14 and 2.5, 1H, axial H of —CH$_2$— in 6); 3.2 to 3.6 (mf, —CH$_2$— and CH<); 3.44 (s, 3H, —OCH$_3$); 6.8 to 7.6 (mt, 19 H aromatic).

Infrared spectrum (KBr), characteristic bands (cm$^{-1}$): 3100–3000, 3000–2850, 2840, 1640, 1600, 1580, 1495, 1450, 1245, 1030, 750, 720, 700.

Use Example 4

0.025 g of 1-hydroxybenzotriazole, 0.27 cm$^3$ of (S)-2-phenylpropanoic acid and 0.32 cm$^3$ of diisopropylamine are added to a suspension of 0.8 g of (3aS,4S,7aS)-7,7-diphenyl-4-(2-methoxyphenyl)-perhydroisoindol-4-ol hydrochloride in 80 cm$^3$ of dry methylene chloride, this solution is subsequently cooled to +5° C. and a suspension of 0.43 g of 1-(3-dimethylaminopropyl)-3-ethyl-carbodiimide hydrochloride in 10 cm$^3$ of dry methylene chloride is rapidly added. The reaction mixture is stirred at +5° C. for 2 hours and at room temperature for 18 hours, washed with 20 cm$^3$ of water and then washed with 20 cm$^3$ of an aqueous saturated solution of sodium chloride (twice), dried over magnesium sulphate and concentrated to dryness under reduced pressure (2.7 kPa). The residue is chromatographed over a Merck silica gel column (particle size 0.04–0.06 mm, diameter 2.8 cm, height 20 cm) by eluting under a pressure of 0.5 bar of nitrogen with a mixture of cyclohexane and ethyl acetate (65/35 by volume) and collecting fractions of 25 cm$^3$. Fractions 6 to 12 are combined and then concentrated to dryness under reduced pressure (2.7 kPa). The redidue is riturated in diisopopyl ether. 0.53 g of (3aS,4S,7aS)-7,7-diphenyl-4-(2-methoxyphenyl)-2-[2-phenyl-(S)-propionyl]-4-perhydroisoindole are obtained in the form of white crystals which melt with decomposition at 128° C.

Use Example 5

0.024 g of 1-hydroxybenzotriazole and 0.33 g of (S)-2-acetyloxy-2-phenylacetic acid are added to a suspension of 0.75 g of (3aS,4S,7aS)-7,7-diphenyl-4-(2-methoxyphenyl)-perhydroisoindol-4-ol hydrochloride in 60 cm$^3$ of dry methylene chloride, this solution is then cooled to +5° C. and a suspension of 0.4 g of 1-(3-dimethylaminopropyl)-3-ethyl-carbodiimide hydrochloride in 20 cm$^3$ of dry methylene chloride is rapidly added, followed by a solution of 0.63 cm$^3$ of diisopropylethylamine in 20 cm$^3$ of dry methylene chloride. The reaction mixture is stirred at +5° C. for 2 hours and at room temperature for 24 hours, diluted with 120 cm$^3$ of methylene chloride, washed with 100 cm$^3$ of water and then with 100 cm$^3$ of an aqueous saturated solution of sodium chloride, dried over magnesium sulphate and concentrated to dryness under reduced pressure (2.7 kPa). The residue is chromatographed over a Merck silica gel column (particle size 0.04–0.06 mm, diameter 2.5 cm, height 39 cm) by eluting under a pressure of 0.5 bar of nitrogen with a mixture of cyclohexane and ethyl acetate (50/50 by volume) and collecting fractions of 60 cm$^3$. Fractions 6 to 10 are combined and then concentrated to dryness under reduced pressure (2.7 kPa). 0.96 g of (3aS,4S,7aS)-7,7-diphenyl-4-(2-methoxyphenyl)-2-[2-acetyloxy-2-phenyl-(S)-acetyl]-perhydroisoindol-4-ol are obtained in the form of a white foam.

Proton NMR spectrum (DMSO d$_6$): at room temperature, a mixture of the two rotamers is found: 1.25 (dmt, J=14, equatorial H of —CH$_2$— in 5); 1.4(dmt, J=14, equatorial H of —CH$_2$— in 5); 2.01 (s, 3H, —OCOCH$_3$); 2.27 (mt, 2H, H of —CH$_2$— in 5 and 1H of —CH$_2$— in 6); 2.65 to 3.6 (mt, —C$_2$— and —CH<); 3.22 (s, 3H, —OCH$_3$); 4.38 (s, OH of one rotamer); 4.86 (s, OH of the other rotamer); 5.66 (s, —CO—CH—O of one rotamer); 5.88 (s, —CO—CH—O of the other rotamer); 6.6 to 7.6 (mt, 19H aromatic).

Infrared spectrum (KBr), characteristic bands (cm$^{-1}$): 3400, 3100–3000, 3000–2850, 2830, 1740, 1660, 1600, 1580, 1495, 1450, 1235, 1050, 755, 700.

1.4 cm$^3$ of an aqueous 1N sodium hydroxide solution and then 10 cm$^3$ of water are added to a solution of 0.8 g of (3aS,4S,7aS)-7,7-diphenyl-4-(2-methoxyphenyl)-2-[2-acetyloxy-2-phenyl-(S)-acetyl]-perhydroisoindol-4-ol in 30 cm$^3$ of ethanol. The reaction mixture is refluxed for 1 hour, concentrated to dryness under reduced pressure (2.7 kPa), taken up in 50 cm$^3$ of water and then 1.5 cm$^3$ of an aqueous 1N hydrochloric acid solution and extracted with 40 cm$^3$ of ethyl acetate (3 times). The organic phases are combined, washed with 50 cm³ of water, dried over magnesium sulphate and concentrated to dryness under reduced pressure (2.7 kPa). The residue is chromatographed over a Merck silica gel column (particle size 0.04–0.06 mm, diameter 2.5 cm, height 27 cm) by eluting under a pressure of 0.4 bar of nitrogen with a mixture of cyclohexane and ethyl acetate (50/50 by volume) and collecting fractions of 30 cm³. Fractions 2 to 5 are combined and concentrated to dryness under reduced pressure (2.7 kPa). The residue is triturated in isopropyl ether. 0.6 g of (3aS,4S,7aS)-7,7-diphenyl-4-(2-methoxyphenyl) -2-[2 -hydroxy-2-phenyl-(S)-acetyl]-perhydroisoindol-4-ol in the form of white crystals which melt at 256°C.

Use Example 6

By working in accordance with Use Example 4, starting from 2.25 g of (3aS,4S,7aS)-7,7-diphenyl-4-(2-methoxyphenyl)-perhydroisoindol-4-ol hydrochloride and 1.25 g of (S)-2-tert-butoxycarbonylamino-2-phenylacetic acid, 0.35 g of (3aS,4S,7aS)-7,7-diphenyl-4-(2-methoxyphenyl)2-[2-tert-butoxycarbonylamino-2 -phenyl-(S)-acetyl]-perhydroisoindol-4-ol are obtained in the form of a white foam.

Proton NMR spectrum (DMSO $d_6$): at room temperature, a mixture of the rotamers is found: 1.3 and 1.4 (2s, —C(CH₃)₃); 1.3 to 1.7 (mt, 1H of —CH₂— in 5); 2.15 to 2.45 (mt, 2H, the other H of —CH₂— in 5 and one H of —CH₂— in 6); 2.7 to 3.7 (mt, —CH₂— and —CH<); 3.33 axed 3.4 (2s, —OCl₃); 4.84 and 5.11 (2s, 1H of NCO—CH—N of the two isomers); 6.6 to 7.7 (mt, 19H aromatic).

Infrared spectrum (KBr), characteristic bands (cm⁻¹): 3580, 3550–3450, 3420, 3100–3000, 3000–2850, 2835, 1710, 1645, 1600, 1580, 1490, 1455, 1395, 1370, 1240, 1170, 1030.

By working in accordance with Example 1, starting from 0.62 g of (3aS,4S,7aS)-7,7-diphenyl-4-(2-methoxyphenyl)-2-[2 -tert-butoxycarbonylamino-2-phenyl-(S)-acetyl] -perhydroisoindol-4-ol, 0.54 g of (3aS, 4S, 7aS )-7,7-diphenyl-4-(2-methoxyphenyl)-2-[2-amino2-phenyl-(S)-acetyl] -perhydroisoindol-4-ol hydrochloride are obtained in the form of a white foam.

Proton NMR spectrum (DMSO $d_6$): a mixture of diastereoisomers is found: 1.34 and 1.53 (2 dmt, J=14, 1H in total, equatorial H of —CH₂— in 5 for the two isomers); 2.31 (mt, 2H, the other H of —CH₂— in 5 and 1H of —CH₂— in 6 ); 2.8 to 3.7 (mt, —CH₂— and —CH< ); 3.36 and 3.42 (2s, 3H, —OCl₃); 4.76 and 4.95 (2s, 1H, NCO—CH—N of the two isomers); 6.6 to 7.7 (mt, 19H aromatic).

Infrared spectrum (KBr), characteristic bands (cm⁻¹): 3425, 3100–3000, 3000–2850, 2830, 3150–2500, 1660, 1600, 1585, 1495, 1450, 1235, 1030, 755, 700.

Use Example 7

0.28 g of carbonyldiimidazole is added to a solution of 0.28 g of (2-methoxyphenyl)-acetic acid in 20 cm³ of dry methylene chloride. The mixture is stirred at room temperature for I hour and a suspension of 0.7 g of (3aS,4S,7aS)-4,7,7-triphenyl-perhydroisoindol-4-ol hydrochloride in 20 cm³ of dry methylene chloride and then 0.48 cm³ of triethylamine are subsequently added in succession. The reaction mixture is stirred at room temperature for 24 hours, diluted with 100 cm³ of methylene chloride, washed with 100 cm³ of water (twice) and then with 100 cm³ of an aqueous saturated solution of sodium chloride, dried over magnesium sulphate and concentrated to dryness under reduced pressure (2.7 kPa). The residue is chromatographed over a Merck silica gel column (particle size 0.04–0.06 mm, diameter 2 cm, height 16 cm) by eluting under a pressure of 0.5 bar of nitrogen with a mixture of cyclohexane and ethyl acetate (55/45 by volume) and collecting fractions of 20 cm³. Fractions 7 to 8 are combined and then concentrated to dryness under reduced pressure (2.7 kPa). The residue is crystallised in 16 cm³ of acetonitrile. The crystals are filtered off and dried. 0.3 g of (3aS,4S,7aS)-4,7,7-triphenyl-2-[(2-methoxyphenyl)-acetyl]-perhydroisoindol-4ol is obtained in the form of white crystals which melt at 236° C.

Use Example 8

By working in accordance with Use Example 4, starting with 1.13 g of (3aS,4S,7aS)-7,7-diphenyl-4-(2-methoxyphenyl)-perhydroisoindol-4-ol hydrochloride and 0.42 g of (2-methoxyphenyl)-acetic acid, 0.61 g of (3aS, 4S, 7aS)-7,7 -diphenyl-4-(2-methoxyphenyl)-2-[(2-methoxyphenyl)-2-[(2 -acetyl]-perhydroisoindol-4-ol is obtained in the form of white crystals which melt at 204° C.

Use Example 9

By working in accordance with Use Example 4, starting from 0.75 g of (3aS,4S,7aS)-7,7-diphenyl-4-(2-methoxyphenyl)-perhydroisoindol-4-ol hydrochloride and 0.28 g of (3-methoxyphenyl)-acetic acid, 0.54 g of (3aS, 4S, 7aS)-7, 7-diphenyl-4-(2-methoxyphenyl)-2-[(3-methoxyphenyl)-acetyl] -perhydroisoindol-4-ol is obtained in the form of white crystals which melt at 185° C.

Use Example 10

By working in accordance with Use Example 4, starting from 0.75 g of (3aS,4S,7aS)-7,7-diphenyl-4-(2 -methoxyphenyl)-perhydroisoindol-4-ol hydrochloride and 0.28 g of (4-methoxyphenyl)-acetic acid, 0.61 g of (3aS, 4S, 7aS)-7, 7-diphenyl-4-(2-methoxyphenyl)-2-[(4-methoxyphenyl)-acetyl] -perhydroisoindol-4-ol is obtained in the form of white crystals which melt at 211° C.

Use Example 11

By working in accordance with Use Example 4, starting from 0.8 g of (3aS,4S,7aS)-7,7-diphenyl-4-(2 -methoxyphenyl)-perhydroisoindol-4-ol hydrochloride and 0.38 g of 1-naphthylacetic acid, 1.16 g of (3aS,4S,7aS)-7,7-diphenyl-4-(2-methoxyphenyl)-2-(1-naphthylacetyl)-perhydroisoindol-4-ol are obtained in the form of a white solid which melts at 225° C.

Use Example 12

By working in accordance with Use Example 4, starting from 0.8 g of (3aS,4S,7aS)-7,7-diphenyl-4-(2 -methoxyphenyl)-perhydroisoindol-4-ol hydrochloride and 0.34 g of 3-thienylacetic acid, 0.53 g of (3aS,4S,7aS)-7,7-diphenyl-4-(2-methoxyphenyl)-2-[(3-thienyl)acetyl]-perhydroisoindol-4-ol is obtained in the form of white crystals which melt with decomposition at 106° C.

Use Example 13

0.41 g of carbonyldiimidazole is added to a solution of 0.44 g of 3-indolylacetic acid in 20 cm³ of dry methylene chloride. The mixture is stirred at room temperature for 1 hour and a suspension of 1.1 g of (3aRS,4RS,7aRS)-7,7-diphenyl-4-(2-methoxyphenyl)-perhydroisoindol-4ol hydrochloride in 25 cm³ of dry methylene chloride and then 0.7 cm³ of triethylamine are subsequently added in succession. The reaction mixture is stirred at room temperature for 24 hours, diluted with 100 cm³ of methylene chloride, washed with 100 cm³ of water (twice) and then with 100 cm³ of an aqueous saturated solution of sodium chloride, dried over magnesium sulphate and concentrated to dryness under reduced pressure (2.7 kPa). The residue is chromatographed over a Merck silica gel column (particle size 0.04–0.06 mm, diameter 2 cm, height 22 cm) by eluting under a pressure of 0.5 bar of nitrogen with a mixture of cyclohexane and ethyl acetate (35/65 by volume) and collecting fractions of 20 cm³. Fractions 7 to 8 are combined and then concentrated to dryness under reduced pressure (2.7 kPa). The residue is triturated in diisopropyl ether. 0.17 g of (3aRS,4RS,7aRS)-7,7-diphenyl-2-(3-indolylacetyl)-4-(2-methoxyphenyl)-perhydroisoindol-4-ol is obtained in the form of a white solid.

Proton NMR spectrum (DMSO $d_6$): 1.48 (d broad, J=14.5, 1H, equatorial H of —CH$_2$— in 5); 2.27 (d broad, J=14.5, 1H, equatorial H of —CH$_2$— in 6); 2.32 (td, J=14.5 and 2, 1H, axial H of —CH$_2$— in 5); 3.02 (td, J=14.5 and 2, 1H, axial H of —CH$_2$— in 6); 2.88 and 3.2 to 3.7 (2 mt, 1H and 5H respectively, —CH$_2$— and —CH); 3.44 (s, 3H, —OCl$_3$); 3.52 (s, 2H, —N—COCH$_2$—); 6.8 to 7.6 (mt, 19H, aromatic).

Infrared spectrum (KBr), characteristic bands (cm⁻1): 3425, 3125–3000, 3000–2850, 1625, 1585, 1490, 1460, 1235, 1030, 745, 700.

Use Example 14

A solution of 0.43 g of 2-(3-indolyl)-2-oxoacetyl chloride in 20 cm³ of dry methylene chloride and then a solution of 0.6 cm³ of triethylamine in 5 cm³ of dry methylene chloride are added successively to a suspension of 0.96 g of (3aS, 4S,7aS)-7,7-diphenyl-4-(2-methoxyphenyl)-perhydroisoindol-4-ol hydrochloride in 25 cm³ Of dry methylene chloride at room temperature, while stirring. The reaction mixture is stirred at this temperature for 24 hours and then diluted with 200 cm³ of methylene chloride, washed with 100 cm³ of an aqueous 1N sodium hydroxide solution and with 50 cm³ of an aqueous saturated solution of sodium chloride, dried over magnesium sulphate and concentrated to dryness under reduced pressure (2.7 kPa). The residue is chromatographed over a Merck silica gel column (particle size 0.04–0.06 mm, diameter 2.5 cm, height 31 cm) by eluting under a pressure of 0.4 bar of nitrogen with a mixture of 1,2-dichloroethane and methanol (70/30 by volume) and collecting fractions of 15 cm³. Fractions 2 to 9 are combined and concentrated to dryness under reduced pressure (2.7 kPa). 1.15 g of (3aS, 4S,7aS)-7,7-diphenyl-2-[2-oxo-2-(3-indolyl)acetyl]-4-(2-methoxyphenyl)-perhydroisoindol-4-ol are obtained in the form of an orange foam.

Infrared spectrum (KBr), characteristic bands (cm⁻¹): 3400, 3250, 3100–3000, 3000–2850, 2835, 1650– 1600, 1580, 1520, 1490, 1455, 1235, 1030, 755, 700.

0.38 g of sodium borohydride is added to a solution of 1.1 g of (3aS,4S,7aS)-7,7-diphenyl-2-[2-oxo-2-(3-indolyl)-(RS)-acetyl]-4-(2-methoxyphenyl)-perhydroisoindol-4-ol in 35 cm³ of ethanol at room temperature, while stirring. The reaction mixture is stirred at this temperature for 4 hours and then treated with 2 cm³ of acetic acid and concentrated to dryness under reduced pressure (2.7 kPa). The residue is dissolved in 100 cm³ of ethyl acetate, the organic phase is washed with 50 cm³ of an aqueous 0.1N sodium hydroxide solution, with 50 cm³ of water and then with 50 cm³ of an aqueous saturated solution of sodium chloride, dried over magnesium sulphate and concentrated to dryness under reduced pressure (2.7 kPa). The residue is chromatographed over a Merck silica gel column (particle size 0.04–0.06 mm, diameter 2.8 cm, height 27 cm) by eluting under a pressure of 0.4 bar of nitrogen with a mixture of 1,2-dichloroethane and methanol (96/4 by volume) and collecting fractions of 10 cm³. Fractions 17 to 31 are combined and concentrated to dryness under reduced pressure (2.7 kPa). The residue is triturated in diisopropyl ether. 0.45 g of (3aS,4S,7aS)-7,7-diphenyl-2-[2-hydroxy-2-(3-indolyl)-(RS)-acetyl]-4-(2-methoxyphenyl)-perhydroisoindol-4-ol is obtained in the form of a white foam.

Proton NMR spectrum (DMSO d6): at room temperature, a mixture of isomers and rotamers is found: 1.4 (mt, 1H, equatorial H of —CH$_2$— in 5); 2.3 (mt, 2H, axial H of —CH$_2$— in 5 and 1H of —CH$_2$— in 6); 2.5 to 3.8 (mt, —CH$_2$— and —CH<); 3.30–3.32–3.35 and 3.38 (4s, OCH$_3$ of the various isomers and rotamers); 5–5.12–5.24 and 5.28 (4s, 1H, N—CO—CH—O of the various isomers and rotamers); 6.5 to 7.8 (mt aromatic).

Infrared spectrum (KBr), characteristic bands (cm ⁻¹): 3420, 3125–3000, 3000–2850, 2830, 1630, 1600, 1580, 1495, 1450, 1235, 1030, 755, 745, 700.

Use Example 15

By working in accordance with the operating method of Use Example 4, starting from 0.8 g of (3aS, 4S, 7aS) -7,7-diphenyl-4-(2-methoxyphenyl)-perhydroisoindol-4-ol hydrochloride and 0.39 g of (5-fluoro-3-indolyl)-acetic acid, 0.36 g of (3aS, 4S, 7aS)-7,7-diphenyl-2-[(5-fluoro-3-indolyl)-acetyl]-4-(2-methoxyphenyl)-perhydroisoindol-4-ol is obtained in the form of white crystals which melt with decomposition at 170° C.

Use Example 16

By working in accordance with Use Example 4, starting from 0.8 g of (3aS,4S,7aS)-7,7-diphenyl-4-(2-methoxyphenyl)-perhydroisoindol-4-ol hydrochloride and 0.41 g of (5-methoxy-3-indolyl)-acetic acid, 0.66 g of (3aS, 4S, 7aS) -7,7-diphenyl-2-[(5-methoxy-3-indolyl)-acetyl]-4-(2-methoxyphenyl)-perhydroisoindol-4-ol is obtained in the form of a beige foam.

Proton NMR spectrum (DMSO $d_6$): 1.5 (d broad, J=14, 1H, equatorial H of —CH$_2$— in 5); 2.29 (d broad, J=14, 1H, equatorial H of —CH$_2$— in 6); 2.35 (td, J=14 and 2.5; axial 1H of —CH$_2$— in 5); 3.04 (td, J=14 and 2.5; axial H of —CH$_2$— in 6); 2.8 to 3.9 (mt, —CH$_2$— and —CH<); 3.44 (s, —OCH$_3$); 3.75 (s, NCO—CH$_2$—); 3.89 (s, 3H, —OCH$_3$ of indole); 6.7 to 7.7 (mt, 18H aromatic); 10.3 (mf, 1H, NH of indole).

Infrared spectrum (KBr), characteristic bands (cm⁻¹): 3300–2200, 3125–3000, 3000–2850, 2830, 1625, 1600, 1580, 1485, 1450, 1230, 1215, 1025, 755, 700.

Use Example 17

By working in accordance with Use Example 4, starting from 0.75 g of (3aS,4S,7aS)-7,7-diphenyl-4-(2methoxyphenyl)-perhydroisoindol-4-ol hydrochloride and 0.32 g of (1-methyl-3-indolyl)-acetic acid, 0.56 g of (3aS, 4S, 7aS) -7,7-diphenyl-4-(2-methoxyphenyl)-2-[(1methyl-3-indolyl)-acetyl] -perhydroisoindol-4-ol is obtained in the form of a beige foam.

Proton NMR spectrum (DMSO $d_6$): at room temperature, a mixture of the two rotamers is found): 1.42 (mt, 1H, 1H of —CH$_2$— in 5); 2.31 (mt, 2H, the other H of —CH$_2$— in 5 and 1H of —CH$_2$— in 6); 2.94 (mt, the other H of —CH$_2$— in 6); 2.7 to 3.6 (mt, —CH$_2$— and —CH<); 3.37 (s, 3H, —OCH$_3$); 3.45 and 3.5 (2s, 2H, —COCH$_2$Ar); 3.72 and 3.78 (2s, 3H, NCH$_3$); 6.8 to 7.7 (mt, 19H aromatic).

Infrared spectrum (KBr), characteristic bands (cm$^{-1}$): 3400, 3125–3000, 3000–2850, 2830, 1637, 1600, 1580, 1485, 1450, 1235, 1050, 750, 700.

Use Example 18

4.2 cm$^3$ of triethylamine and then 2.4 g of (2-methoxyphenyl)-acetyl chloride in 50 cm$^3$ of methylene chloride are added to a solution of 4.5 g of (3aRS, 4RS, 5RS, 7aRS)-7,7-diphenyl-4-(2-methoxyphenyl)-perhydroisoindole-4, 5-diol hydrochloride in 100 cm$^3$ of methylene chloride, cooled to 0° C. The reaction mixture is stirred at room temperature for 90 minutes; it is washed with twice 10 cm$^3$ of water, dried over magnesium sulphate and concentrated to dryness under reduced pressure (2.7 kPa). The solid which has crystallised out is taken up in 100 cm$^3$ of diisopropyl ether and then filtered off and washed with 50 cm$^3$ of a saturated solution of sodium bicarbonate and then 50 cm$^3$ of diisopropyl ether. 4.35 g of (3aRS,4RS,5RS,7aRS)-7,7-diphenyl-4-(2-methoxyphenyl)-2-[(2-methoxyphenyl)-acetyl]-perhydroisoindole-4,5-diol are obtained in the form of a light beige solid which melts at 278° C.

(2-Methoxyphenyl)-acetyl chloride is obtained from a mixture of 2.2 g of (2-methoxyphenyl)-acetic acid and 20 cm$^3$ of thionyl chloride, which is refluxed for 30 minutes. After concentrating to dryness under reduced pressure (2.7 kPa), 2.4 g of a yellow oil, which is used in the crude state in the subsequent syntheses, are obtained.

Use Example 19

By working in accordance with Use Example 18, starting from 0.5 g of (3aS,4S,5S,7aS)-7,7-diphenyl-4 -phenyl-perhydroisoindole-4,5-diol hydrochloride and 0.39 g of (2-methoxyphenyl)-acetic acid, 0.4 g of (3aS,4S,5S,7aS)-7,7-diphenyl-4-phenyl-2-[(2 -methoxyphenyl)-acetyl]-perhydroisoindole-4,5-diol is obtained in the form of a white solid which melts with decomposition at 150° C.

Use Example 20

By working in accordance with Example 1, starting from 0.5 g of (3aS,4S,5S,7aS)-7,7-diphenyl-4 -phenyl-perhydroisoindole-4,5-diol hydrochloride and 0.25 g of (S)-2-(2 -methoxyphenyl)-propionic acid, 0.52 g of (3aS, 4S, 5S, 7aS)-7,7-diphenyl-4-phenyl-2-[-2-(2 -methoxyphenyl)-(S)-propionyl]-perhydroisoindole-4,5 diol is obtained in the form of a white solid which melts with decomposition at 158° C.

Use Example 21

0.46 g of 1-(3-dimethylaminopropyl)-3-ethylcarbodiimide and 0.34 cm$^3$ of diisopropylamine are added to a solution of 0.9 g of (3aRS,4RS,5RS,7aRS)-7,7 -diphenyl-4-(2-methoxyphenyl)-perhydroisoindole-4,5-diol hydrochloride, 0.4 g of 3-indolylacetic acid and 20 mg of 1-hydroxybenzotriazole hydrate in 90 cm$^3$ of methylene chloride, cooled to 0° C. The mixture is stirred at room temperature for 15 hours, acidified with 0.1N HCl and then taken up in an aqueous saturated solution of sodium chloride. The organic phase is decanted, dried over magnesium sulphate and concentrated to dryness under reduced pressure (2.7 kPa). The foam obtained is recrystallised in 10 cm$^3$ of boiling acetonitrile. 0.85 g of (3aRS,4RS,5RS,7aRS)-7,7-diphenyl-4-(2-methoxyphenyl)-2-(3-indolylacetyl)-perhydroisoindole-4,5 -diol is obtained in the form of a white solid which melts at 266° C.

Use Example 22

0.1 cm$^3$ of triethylamine and then 0.04 cm$^3$ of phenylacetyl chloride are added to a suspension of 0.14 g of (3aS,4S,7aS)-7,7-diphenyl-4-fluoro-4-(2 -methoxyphenyl)-perhydroisoindole hydrochloride in 7 cm$^3$ of dry methylene chloride at room temperature. The reaction mixture is stirred at this temperature for 5 hours, diluted with 100 cm$^3$ of methylene chloride, washed with 40 cm$^3$ of a saturated solution of sodium bicarbonate and then with 40 cm$^3$ of water, dried over magnesium sulphate and concentrated to dryness under reduced pressure (2.7 kPa). The residue obtained is triturated in diisopropyl ether. 0.1 g of (3aS,4S,7aS)-7,7 -diphenyl-4-fluoro-4-(2-methoxyphenyl )-2 -phenylacetyl-perhydroisoindol-4-ol is obtained in the form of a white foam.

Proton NMR spectrum (DMSO D$_6$): at room temperature, a mixture of rotamers is found: 1.62 (mt, 1H, 1H of —CH$_2$— in 5); 2 to 3.8 (mt, —CH$_2$— and —CH<); 3.38 and 3.42 (2s, 3H, —OCH$_3$); 6.7 to 7.6 (mt, 19H, aromatic).

Infrared spectrum (KBr), characteristic bands (cm$^{-1}$): 3100–3000, 3000–2850, 2840, 1640, 1600, 1580, 1495, 1455, 1240, 1030, 755, 720, 700.

Use Example 23

1.5 cm$^3$ of triethylamine and then 1.6 g of (2-methoxyphenyl)-acetyl chloride are added to a solution of 1.5 g of (3aS,7aR)-4,4-diphenyl-7-(2-methoxyphenyl)-2,3,3a,4,5, 7a-hexahydro-isoindole hydrochloride in 20 cm$^3$ of methylene chloride, cooled to 0° C. The mixture is stirred at room temperature for 15 hours; the reaction mixture is washed with twice 40 cm$^3$ of water, dried over magnesium sulphate and concentrated to dryness under reduced pressure (2.7 kPa). The residue is chromatographed over a Merck silica gel column (particle size 0.04–0.06 mm, diameter 3.6 cm, height 25 cm) by eluting under a pressure of 0.5 bar of nitrogen with a mixture of cyclohexane and ethyl acetate (75/25 by volume) and collecting fractions of 25 cm$^3$. Fractions 14 to 28 are combined and concentrated to dryness under reduced pressure (2.7 kPa). The yellow foam obtained is recrystallised from 10 cm$^3$ of cyclohexane to give 0.38 g of (3aS,7aR)-4,4-diphenyl-2-[(2-methoxyphenyl)-acetyl]-7-(2 -methoxyphenyl)-2,3,3a,4,5,7a-hexahydro-isoindole in the form of a beige solid which melts at 142° C.

Use Example 24

By working in accordance with Use Example 4, but starting from 2 g of (3aS,4S,7aS)-7,7-diphenyl-4-(2-methoxyphenyl)-perhydroisoindol-4-ol hydrochloride and 0.96 g of 3-indolylacetic acid, 2.17 g of (3aS,4S,7aS)-7,7-diphenyl-4-(2-methoxyphenyl)-2-[(3 -indolyl)-acetyl]-perhydroisoindol-4-ol are obtained in the form of white crystals which melt at 142° C.

Use Example 25

By working in accordance with Use Example 4, but starting from 0.73 g of (3aS,4S,7aS)-7,7-diphenyl-4 -(2-methoxyphenyl)-perhydroisoindol-4-ol hydrochloride and 0.5 g of (S)-2-(2-benzyloxyphenyl)-propionic acid, 0.73 g of (3aS,4S,7aS) -7,7-diphenyl-4-(2-methoxyphenyl)-2 -2-[2-(2-benzyloxyphenyl)-(S)-propionyl]-perhydroisoindol-4-ol is obtained in the form of a white foam.

Proton NMR spectrum (DMSO $d_6$): at room temperature, a mixture of the rotamers is found: 1.15 (2d, 3H of $CH_3$—CH); 3.35 (2s, 3H of $OCH_3$); 3.98 and 3.78 (2q, 1H of CH—$CH_3$); 4.2 (s, 1H of OH); 4.6 to 5 (2dd, 2H of $CH_2O$); 6.7 to 7.6 (m, 23H aromatic).

0.005 g of 10% palladium-on-charcoal is added to a solution of 0.73 g of (3aS,4S,7aS)-7,7-diphenyl-4-(2-methoxyphenyl)-2-[2-(2-benzyloxyphenyl)-(S)propionyl]-perhydroisoindol-4-ol obtained above in 20 cm³ of absolute ethanol, and hydrogen is bubbled into the reaction mixture at room temperature for 2 hours. The reaction mixture is filtered over celite and then concentrated to dryness under reduced pressure (2.7 kPa). The residue is chromatographed over a Merck silica gel column (particle size 0.04–0.06 mm, diameter 2.4 cm, height 20 cm) by eluting under a pressure of 0.5 bar of nitrogen with a mixture of cyclohexane and ethyl acetate (80/20 by volume) and collecting fractions of 30 cm³. Fractions 3 to 8 are combined and concentrated to dryness under reduced pressure (2.7 kPa). 0.2 g of (3aS,4S,7aS)-7,7-diphenyl-4-(2 -methoxyphenyl)-2-[2-(2-hydroxyphenyl)-(S)-propionyl]- perhydroisoindol-4-ol are obtained in the form of white crystals which melt at 150° C. with decomposition.

(S)-2-(2-Benzyloxyphenyl)-propionic acid can be obtained in the following manner:

A solution of 1.07 g of (1R,2S)-N-[(S)-2-(2 -benzyloxyphenyl)-propionyl]-2,10-camphor-sultam in a mixture of 0.47 cm³ of an aqueous 30% strength solution of sodium hydroxide and 10 cm³ of tetrahydrofuran is stirred at room temperature for 48 hours. The reaction mixture is concentrated to dryness under reduced pressure (2.7 kPa) and then diluted with 20 cm³ of distilled water, the aqueous phase is extracted with 25 cm³ of methylene chloride, subsequently acidified with 3 cm³ of an aqueous 37% strength solution of hydrochloric acid and finally extracted 3 times with 25 cm³ of methylene chloride. The organic phase is dried over magnesium sulphate and concentrated to dryness under reduced pressure (2.7 kPa). 0.5 g of (S)--2-(2-benzyloxyphenyl)-propionic acid is obtained in the form of a colourless oil.

Proton NMR spectrum ($CDCl_3$): 1.5 (d, 3H of $CH_3$—CH); 4.18 (q, 1H of CH—$CH_3$); 5.1 ($A_2$, 2H of $OCH_2$); 6.95 to 7.45 (m, 9H aromatic).

(1R,2S)-N-[(S)-2-(2-Benzyloxyphenyl)-propionyl]-2,10-camphor-sultam can be prepared in the following manner:

1.62 g of potassium tert-butylate are added in fractions to a solution of 4.1 g of (1R,2S)-N-[(2 -benzyloxyphenyl)-acetyl]-2,10-camphor-sultam in 40 cm³ of tetrahydrofuran, cooled to −78° C., and a solution of 2.63 cm³ of methyl iodide in 2 cm³ of tetrahydrofuran is then added dropwise to this suspension. The reaction mixture is stirred at −78° C. for 18 hours and 40 cm³ of an aqueous saturated solution of ammonium chloride are then added. After returning to room temperature, the reaction mixture is extracted with 80 cm³ of ethyl acetate and the organic phase is washed twice with 25 cm³ of an aqueous saturated solution of ammonium chloride, dried over magnesium sulphate and concentrated to dryness under reduced pressure (2.7 kPa). The residue is chromatographed over a Merck silica gel column (particle size 0.04–0.06 mm, diameter 4 cm, height 39 cm) by eluting under a pressure of 0.3 bar of nitrogen with methylene chloride and collecting fractions of 25 cm³. Fractions 21 to 53 are combined and concentrated to dryness under reduced pressure (2.7 kPa). The residue is recrystallised from diisopropyl ether. 1.1 g of (1R,2S)-N-[(S)-2-(2 -benzyloxyphenyl)-propionyl]-2,10-camphor-sultam are obtained in the form of white crystals which melt at 131° C.

(1R,2S)-N-[(2-benzyloxyphenyl)-acetyl]-2,10 -camphor-sultam can be prepared in the following manner:

A solution of 0.74 g of sodium hydroxide in 20 cm³ of distilled water and then 0.03 cm³ of Aliquat 336® are added dropwise to a solution, cooled to +10° C., of 3.23 g of (1R,2S)-2,10-camphor-sultam in 16 cm³ of dry methylene chloride. A solution of 3.9 g of (2-methoxyphenyl)-acetyl chloride in 5 cm³ of methylene chloride is then added dropwise at +10° C. The reaction mixture is stirred at +10° C. for 1 hour and decanted, the aqueous phase is extracted with 80 cm³ of methylene chloride and the organic phases are combined, washed with 80 cm³ of distilled water, dried over magnesium sulphate and concentrated to dryness under reduced pressure (2.7 kPa). The residue is crystallised in 15 cm³ of diisopropyl ether. 4.1 g of (1R,2S)-N-[(2 -benzyloxyphenyl)-acetyl]-2,10-camphor-sultam are obtained in the form of white crystals which melt at 116° C.

Use Example 26

By working in accordance with Use Example 4, but starting from 12.27 g of 7,7-diphenyl-4-(2 -methoxyphenyl)-perhydroisoindol-4-ol hydrochloride and 7.88 g of (2-benzyloxyphenyl)-acetic acid, 16.4 g of (3aS,4S,7aS)-7,7-diphenyl-4-(2-methoxyphenyl)-2-[(2 -benzyloxyphenyl)-acetyl]-perhydroisoindol-4-ol are obtained in the form of a white foam.

Proton NMR spectrum (DMSO d6): at room temperature, a mixture of the rotamers was found: 3.4 (s, 3H Of $OCH_3$); 5 (s, 2H of —$CH_2O$); 6.85 to 7.5 (m, 23H aromatic).

By working in accordance with Use Example 25, starting from 16.4 g of (3aS,4S,7aS)-7,7-diphenyl-4-(2methoxyphenyl)-2 -[2-(2-benzyloxyphenyl)-acetyl] -perhydroisoindol-4-ol, 11.4 g of (3aS,4S,7aS)-7,7-diphenyl-4 -(2-methoxyphenyl)-2-[2-(2-hydroxyphenyl)acetyl]-perhydroisoindol-4-ol are obtained in the form of white crystals which melt at 190° C.

Use Example 27

0.16 g of 1-hydroxybenzotriazole, 2.59 g of (S)-2-(2-methoxyphenyl)-propionic acid and 2.08 cm³ of diisopropylethylamine are added to a suspension of 5 g of (3aS, 7aR)-4,4-diphenyl-7-(2-methoxyphenyl)-2,3,3a,4,5,7a-(1H)-hexahydroisoindole hydrochloride in 70 cm³ of dry methylene chloride, this solution is then cooled to +5° C. and a suspension of 2.8 g of 1-(3 -dimethylaminopropyl)-3-ethyl-carbodiimide hydrochloride in 10 cm³ of dry methylene chloride is added rapidly. The reaction mixture is stirred at +5° C. for 2 hours and then at room temperature for 24 hours, washed with 20 cm³ of water and then with 20 cm³ of an aqueous saturated solution of sodium chloride (twice), dried over magnesium sulphate and concentrated to dryness under reduced pressure (2.7 kPa). The residue is chromatographed over a Merck silica gel column (particle size 0.04–0.06 mm, diameter 4 cm, height 20 cm) by eluting under a pressure of 0.5 bar of nitrogen with a mixture of cyclohexane and ethyl acetate (80/20 by volume) and collecting fractions of 50 cm³. Fractions 2 to 8 are combined and concentrated to dryness under reduced pressure (2.7 kPa). The residue is triturated in diisopropyl ether. 4.43 g of (3aS, 7aR) -4,4 -diphenyl-7-(2-methoxyphenyl)-2-[2-(2 -methoxyphenyl-(S)-propionyl]-2,3,3a, 4,5,7a-(1H)-hexahydroisoindole are obtained in the form of white crystals which melt at 104° C. with decomposition.

Use Example 28

30 mg of 1-hydroxybenzotriazole hydrate, 0.66 g of 1-(3-dimethylaminopropyl)-3-ethylcarbodiimide and 0.6 cm³ of diisopropylethylamine are added to a solution of 1.1 g of (3aS,4S,5S,7aS)-7,7-diphenyl-4 -(2-methoxyphenyl)-perhydroisoindole-4,5 -diol and 0.58 g of (S)-2-(2-methoxyphenyl)-propanoic acid in 30 cm³ of methylene chloride, cooled to 0° C. The mixture is stirred at room temperature for 3 hours and 30 minutes and 100 cm³ of water and 50 cm³ of an aqueous saturated solution of sodium chloride are added. The organic phase is decanted, dried over magnesium sulphate and concentrated to dryness under reduced pressure (2.7 kPa). The yellow residue obtained is chromatographed over a Merck silica gel column (particle size 0.04–0.06 mm, diameter 2 cm, height 30 cm) by eluting under a pressure of 0.5 bar of nitrogen with a mixture of cyclohexane and ethyl acetate (60/40 by volume) and collecting fractions of 25 cm³. Fractions 6 to 14 are combined and then concentrated to dryness under reduced pressure (2.7 kPa). 0.9 g of (3aS,4S,5S,7aS)-7,7-diphenyl-4-(2 -methoxyphenyl)-2-[2-(2-methoxyphenyl)-(S)-propionyl] -perhydroisoindole-4,5-diol which melts at 256° C. is obtained.

Use Example 29

(3aRS, 4RS, 5RS, 7aRS)-7,7-Diphenyl-4-(2-methoxyphenyl)-2 -[(2-benzyloxyphenyl)-acetyl ]-perhydroisoindole-4,5-diol is prepared by the operating method of Use Example 28 starting from 1.24 g of (3aRS, 4RS, 5RS, 7aRS) -7,7 -diphenyl-4-(2-methoxyphenyl) -perhydroisoindole-4,5-diol and 0.8 g of (2-benzyloxy)phenylacetic acid. 1.7 g of (3aRS,4RS,5RS,7aRS)-7,7-diphenyl-4 -(2-methoxyphenyl)-2-[(2-benzyloxyphenyl)acetyl]-perhydroisoindole-4,5-diol which melts at 158° C. are obtained.

A mixture of 1.5 g of (3aRS,4RS,5RS,7aRS)-7,7 -diphenyl-4-(2-methoxyphenyl)-2-[(2-benzyloxyphenyl)-acetyl] -perhydroisoindole-4,5-diol and 50 cm³ of ethanol is heated at 60° C, while stirring; 0.5 g of 20% palladium hydroxide-on-charcoal is added and the reaction mixture is then hydrogenated at a temperature of 60° C. under atmospheric pressure, while stirring. After a reaction time of 45 minutes, the theoretical volume of hydrogen has been absorbed; the reaction mixture is filtered and then concentrated to dryness under reduced pressure (2.7 kPa). The residue is crystallised from 20 cm³ of isopropyl ether. 0.8 g of (3aRS, 4RS, 5RS, 7aRS) -7,7-diphenyl-4-(2-methoxyphenyl)-2 -2-[(2-hydroxyphenyl)-acetyl]-perhydroisoindole-4,5diol which melts at 188°–190° C. is obtained.

Use Example 30

By working in accordance with the operating method of Use Example 21, starting from 0.62 g of (3aRS, 4RS, 5RS, 7aRS)-7,7 -diphenyl-4-(2-methoxyphenyl)-perhydroisoindole- 4,5-diol and 0.30 g of (2-dimethylamino) phenylacetic acid, 0.47 g of (3aRS, 4RS, 5RS, 7aRS )-7,7-diphenyl-4-(2-methoxyphenyl )- 2[(2-dimethylaminophenyl)-acetyl]-perhydroisoindole-4,5 diol which melts at 250° C. is obtained.

Use Example 31

By working in accordance with the operating method of Use Example 21, starting from 1.04 g of (3aS, 4S, 5S, 7aS) -7,7-diphenyl-4-(2-methoxyphenyl)-perhydroisoindole 4,5-diol and 0.49 g of 3-indolylacetic acid, 1.25 g of (3aS,4S, 5S,7aS)-7,7-diphenyl -4-(2-methoxyphenyl)-2-(3-indolylacetyl)-perhydroisoindole-4,5 -diol which melts at 210° C. are obtained.

Use Example 32

By working in accordance with the operating method of Use Example 21, starting from 0.62 g of (3 aRS, 4RS, 5RS, 7 aRS )-7,7 -diphenyl-4-(2-methoxyphenyl)-perhydroisoindole-4,5 -diol and 0.31 g of (N-methyl-3indolyl) -acetic acid, 0.55 g of (3aRS, 4RS, 5RS, 7aRS)-7,7 -diphenyl-4-(2-methoxyphenyl)-2-[(N-methyl-3-indolyl)-acetyl] -perhydroisoindole-4,5 -diol which melts at 240° C. is obtained.

Although the present invention has been described in conjunction with specific embodiments, it is evident that may alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A perhydroisoindole derivative of formula:

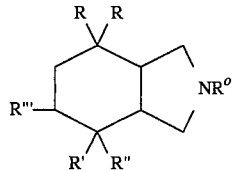

in which:

the symbols R are identical and represent phenyl radicals which are optionally substituted by a halogen atom or by a methyl radical in position 2 or 3, the symbol R' represents a phenyl radical which is optionally substituted in position 2 by a alkyl or alkyloxy radical containing 1 to 2 carbon atoms, the symbol R" represents a fluorine atom or a hydroxyl radical and the symbol R''' represents a hydrogen atom, or the symbols R" and R''' represent hydroxyl radicals, or the symbol R" forms a bond with R''', and the symbol $R^o$ represents a hydrogen atom or represents a protective radical, in the racemic form, in its stereoisomeric forms having the structure:

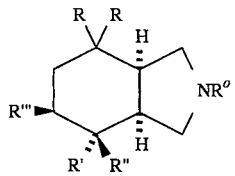

wherein R, R', R", R''' and $R^o$ are as defined above, or in the form of a mixture, as well as its salts, thereof.

2. A perhydroisoindole derivative according to claim 1, wherein:

the symbols R are identical and represent phenyl radicals, the symbol R' represents a phenyl radical which is optionally substituted in position 2 by an alkyl or alkyloxy radical containing 1 or 2 carbon atoms, the symbol R" represents a fluorine atom or a hydroxyl radical and the symbol R''' represents a hydrogen atom, or the symbols R" and R"' represent hydroxyl radicals, or the symbol R" forms a bond with R"', and the symbol $R^o$ represents a hydrogen atom or represents a benzyl or t-butoxycarbonyl radical.

3. A perhydroisoindole derivative according to claim 1, wherein it is: 7,7-diphenyl-4-(2-methoxyphenyl)-2-tert-butoxycarbonyl-perhydroisoindol-4-ol; 7,7-diphenyl-4-(2-methoxyphenyl)-perhydroisoindole-4-ol; 7,7-diphenyl-4-(2-methoxyphenyl-2-tert-butoxycarbonyl-perhydroisoindole-4,5-diol; 7,7-diphenyl-4-(2-methoxphenyl)-perhydroisoindole-4,5-diol; and 2-benzyl-7,7-diphenyl-4-(2-methoxyphenyl)-perhydroisoindole-4,5-diol.

4. A perhydroisoindole derivative according to claim 1, wherein the derivative is selected from the group consisting of 7,7-diphenyl-4-(2-methoxphenyl)-2-tert-butoxycarbonyl-perhydroiso-indol-4-ol; 7,7-diphenyl-4-(2-methoxyphenyl)-perhydroisoindol-4-ol; 7,7-diphenyl-4-(2-methoxyphenyl-2-tert-butoxycarbonyl-perhydroisoindole-4,5-diol; 7,7-diphenyl-4-(2-methoxyphenyl)-perhydroisoindole-4,5-diol; and 2-benzyl-7,7-diphenyl-4-(2-methoxyphenyl)-perhydroisoindole-4,5-diol.

\* \* \* \* \*

UNITED STATES PATENT AND TRADEMARK OFFICE
CERTIFICATE OF CORRECTION

PATENT NO. : 5,463,077
DATED : October 31, 1995
INVENTOR(S) : Daniel ACHARD et al.

It is certified that error appears in the above-indentified patent and that said Letters Patent is hereby corrected as shown below:

Title page, item [56], after "Attorney, Agent, or Firm—", "Morgan & Finnegan" should read --Finnegan, Henderson, Farabow, Garrett & Dunner--.

Title page, item [57], in the Abstract, line 1, "ivention" should read --invention--.

Claim 1, column 28, line 37, "a alkyl" should read --an alkyl--.

Claim 3, column 29, line 8, "perhydroisoindole" should read --perhydroisoindol--.

Claim 3, column 29, line 10, "(2-methoxphenyl)" should read --(2-methoxyphenyl)--.

UNITED STATES PATENT AND TRADEMARK OFFICE
CERTIFICATE OF CORRECTION

PATENT NO. : 5,463,077
DATED : October 31, 1995
INVENTOR(S) : Daniel ACHARD et al.

It is certified that error appears in the above-indentified patent and that said Letters Patent is hereby corrected as shown below:

Claim 4, column 30, line 3, "(2-methoxphenyl)" should read --(2-methoxyphenyl)--.

Claim 4, column 30, line 4, "perhydroiso-indol" should read --perhydroisoindol--.

Signed and Sealed this

Fifth Day of August, 1997

Attest:

BRUCE LEHMAN

Attesting Officer

Commissioner of Patents and Trademarks